(12) United States Patent
Kobayashi et al.

(10) Patent No.: US 7,956,026 B2
(45) Date of Patent: Jun. 7, 2011

(54) CLEANING AGENT

(75) Inventors: Shunsuke Kobayashi, Chiba (JP); Yoshiyuki Hayashi, Otsu (JP); Yasushi Nakaida, Narita (JP); Shin Nakae, Chiba (JP); Makoto Kageyama, Sodegaura (JP); Kiyoji Miyagishi, Chiba (JP)

(73) Assignee: ESPO Chemicals Corp., Chiba (JP)

( * ) Notice: Subject to any disclaimer, the term of this patent is extended or adjusted under 35 U.S.C. 154(b) by 55 days.

(21) Appl. No.: 12/663,038

(22) PCT Filed: Jun. 4, 2008

(86) PCT No.: PCT/JP2008/060266
§ 371 (c)(1),
(2), (4) Date: Dec. 4, 2009

(87) PCT Pub. No.: WO2008/149884
PCT Pub. Date: Dec. 11, 2008

(65) Prior Publication Data
US 2010/0216686 A1  Aug. 26, 2010

(30) Foreign Application Priority Data
Jun. 4, 2007 (JP) .................................. 2007-147675

(51) Int. Cl.
*C11D 3/32* (2006.01)
*C11D 3/37* (2006.01)
*C11D 3/43* (2006.01)
*C11D 3/48* (2006.01)

(52) U.S. Cl. ........ 510/480; 510/263; 510/271; 510/382; 510/384; 510/475; 510/499

(58) Field of Classification Search .................. 510/263, 510/271, 382, 384, 475, 480, 499
See application file for complete search history.

(56) References Cited

U.S. PATENT DOCUMENTS

| | | | |
|---|---|---|---|
| 5,424,041 A | 6/1995 | Kishimoto | |
| 6,884,766 B2 * | 4/2005 | DeClercq et al. | 510/322 |

FOREIGN PATENT DOCUMENTS

| JP | 2775162 B2 | 6/1990 |
|---|---|---|
| JP | 05-131020 | 5/1993 |
| JP | 05-322218 | 12/1993 |
| JP | 2132366 B | 8/1994 |
| JP | 2134708 B | 8/1994 |
| JP | 7216389 A | 8/1995 |
| JP | 2001-149739 A | 6/2001 |
| JP | 02-256030 | 9/2002 |
| JP | 04-250331 | 9/2004 |
| JP | 04-313893 | 11/2004 |
| JP | 2004-313983 A | 11/2004 |
| JP | 2007-45732 A | 2/2007 |

OTHER PUBLICATIONS

International Search Report for PCT/JP2008/060266 (in Japanese and in English).
Written Opinion of the International Searching Authority for PCT/JP2008/060266 (in Japanese and in English).

* cited by examiner

*Primary Examiner* — Brian P Mruk
(74) *Attorney, Agent, or Firm* — Hoffmann & Baron, LLP

(57) ABSTRACT

The present invention herein provide a cleaning agent which comprises (A) an aqueous solution or an aqueous dispersion containing a linear poly(meth)acrylamide having an average molecular weight of not less than $5 \times 10^6$ as determined according to the intrinsic viscosity-determining technique in a concentration ranging from 0.0001 to 0.01% by mass; (B) a poly(hexamethylene-biguanide) hydrochloride represented by the following general formula (1); and (C) at least one compound selected from the group consisting of propylene glycol, dipropylene glycol, tripropylene glycol, diethylene glycol, triethylene glycol, tetraethylene glycol, and ethers of ethylene glycol and propylene glycol with alcohols each having 1 to 3 carbon atoms, and esters thereof with fatty acids each having 1 to 3 carbon atoms, glycine and taurine:

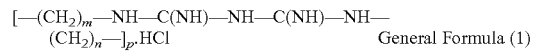

General Formula (1)

wherein m and n each represent an integer ranging from 2 to 5 and p is an integer ranging from 5 to 16.

15 Claims, No Drawings

CLEANING AGENT

CROSS-REFERENCE TO RELATED APPLICATIONS:

This application is the National Stage of International Application No. PCT/JP2008/060266, filed Jun. 4, 2008, which claims the benefit of Japanese Application No. 2007-147675, filed Jun. 4, 2007, the contents of which are incorporated by reference herein.

FIELD OF THE INVENTION

The present invention relates to a cleaning agent and more particularly to a cleaning agent for separating and removing contaminants present, in particular, in the air or atmosphere within the living and working spaces and in other gases as well as on the surface of objects in the form of, for instance, molecules, aerosols and oily adhesive hardened films. These various contaminants are suspended in, adhered to or absorbed on the foregoing gases and objects and they may exert mortal, acute, subacute, chronic or transient adverse effects on the health of human beings and other animals when they absorb such contaminants and/or come in close contact therewith, they may thus give them unpleasant feelings and they may cause environmental pollution through the discharge, leakage and/or accumulation thereof.

BACKGROUND OF THE INVENTION

To make, clean, the surface of an object on which contaminating gases or contaminants are adhered, there have been adopted a variety of methods depending on a variety of factors such as the kinds and particle sizes of such contaminants, the concentration of the contaminants in a gas, the mobility and flow rate of the contaminants or the gas, and the hydrophilicity and hydrophobicity of the contaminants, and the boiling points and reactivity thereof.

However, these methods each suffer from various problems and they also have limits in their applications.

The typical thereof will be listed below (methods (1) to (15)):

(1) Combustion Method: This method comprises the steps of combusting the exhaust gas containing VOC, which is discharged from a large-scale factory, and then externally discharging the combustion gas. There have conventionally been adopted, for instance, the direct combustion technique, the catalytic combustion technique, and the accumulative-combustion technique. However, a large quantity of fuels such as LPG should be used to remove contaminants such as organic solvents present in an exhaust gas having a large volume in a low concentration. This results in the external discharge of carbon dioxide in a high concentration, which may become a cause of the global warming. In addition, the mist of oily paints and varnishes and gravure inks cannot completely be burned and the exhaust gas emitted through the combustion thereof may give out an intensive bad smell and accordingly, this technique should be accompanied by a deodorizing treatment of the exhaust gas, in most of cases, which is fundamentally unnecessary.

(2) Method for the Adsorption of Contaminants Using Porous Material: This is a method in which contaminants are adsorbed on the layer of a porous adsorbent such as activated carbon or zeolite. This technique would certainly permit the removal of molecular contaminants and the adsorbents are reused over about 10 times by expelling the contaminants adsorbed on the adsorbents out of the used ones (which would undergo breakthrough) through the use of high temperature steam to thus regenerate the same. However, there has not yet been established any satisfactory technique for recovering the contaminants expelled therefrom without externally discharging the same. Moreover, the use of such adsorbent suffers from a problem in that they show loadings or clogging to such an extent that the regeneration thereof is impossible any more, in case where the contaminated gas contains, for instance, various kinds of tar-like substances and mist of paints and varnishes, having large particle sizes. The use of zeolite suffers from the same problems and the zeolite likewise suffers from the problem of causing immediate breakthrough and deactivation.

(3) Photo-catalytic Method: This is a technique in which the titanium oxide-coated surface is irradiated with light rays. There have been proposed a variety of specific techniques of this type. However, these techniques suffer from such problems that the gaseous contaminants are quite slowly be decomposed, the decontamination effect thereof is reduced when the catalyst surface becomes dirty and they can thus be used in only considerably limited applications.

(4) Ozone Oxidation Method: This is a method quite suitable for the sterilization and deodorization of the tap water and the method has an immediate cleaning effect when applying it to the cleaning of the space impregnated with filthy odors. However, the following drawbacks arise, such that ozone is strongly toxic, that the use thereof is not adapted for the treatment of the exhaust present in, for instance, a wide space in a factory, that the use of ozone is limited in the place and time and that the use thereof causes damages of utensils and implements.

(5) Existing Dust-Collecting method: There have widely been used, for instance, a bag-filtering technique in which a heavy and fine canvas is used and dust is collected while making use of, for instance, the gravity, the centrifugal force and the force of inertia; the electric dust-precipitating technique which makes use of an electrostatic attractive force; and the dust-collection method through filtration, which makes use of porous powdery materials. These methods are effective for the removal of, for instance, non-adhesive dust particles having a particle size of not less than 0.01 μm, but they are ineffective for the removal of, for instance, viruses having a particle size of less than 0.01 μm, adhesive aerosols such as the smoke of tobacco and gaseous contaminants.

(6) Method Using Perfumes and/or Aromatics: The masking technique, in which unpleasant odors and irritative odors emitted from chemicals are organoleptically relieved through the use of an aromatic, has widely been put into practice by the use of an aerosol type spraying can or a plastic pump. The ability of most of these products to remove dust and the ability thereof to deodorize have not yet been completely and scientifically demonstrated or elucidated and most of the guests of a hotel have a dislike to the smells of a perfume adsorbed on the whole wall surface of a guest room, which are diffused, little by little, therefrom. In addition, this method has been proved to be ineffective for the odors, whose complete elimination has considered to be impossible, such as the odor of a cigar, that of the incense, the offensive smell of the armpit whose principal components are lower fatty acids, the evil smell of the body, the smell of formaldehyde, the smell of insecticides and the smell of VOC included in, for instance, paints and varnishes, in addition to the foregoing smells of the perfumes.

(7) Method Which Makes Use of Plant's Extracts: There has been known a method which makes use of a commercially available liquid product comprising a plant extract named catechin or flavonoid type component-containing extract. The extracts containing catechin derived from green tea are effective for the deodorization of perishable or flesh foods. However, they are limited in their applications, they are ineffective for the deodorization of the decomposition products of food waste products having complicated compositions and the use of such an extract may rather result in the secondary environmental pollution due to the mixed odors thereof in most of cases.

(8) Method Using Wood-Derived Vinegar or Bamboo-Derived Vinegar: This is a method which makes use of vinegar obtained, as a by-product, when producing wood-derived or bamboo-derived charcoal through the carbonization of wood or bamboo, for the deodorization. These wood-derived and bamboo-derived vinegars are sometimes sold in the form of an all-round deodorant and a health beverage, which are friendly to the environment, but they contain harmful components such as methanol, formic acid and other lower fatty acids, lower aldehydes and tars having various compositions; mutagenic components; and the components suspected as carcinogens, and they do not show any deodorant effect even when using them for the deodorization of the interior, for instance, for the elimination of the smells of tobacco. On the contrary, if they are applied onto the construction materials, it would be needed, in some cases, to eliminate the irritative odors emitted from these materials.

(9) Scrubber-Cleaning Method Using Existing Aqueous Cleaning Agent: There have widely been used, in this technique, various compounds such as sulfuric acid, caustic soda, chlorates, composites of ascorbic acid and ferrous salts and sulfites. These cleaning liquids are effective for gaseous contaminants having simple compositions and rich in the chemical reactivity, but any single kind of compound never permits the elimination of complex gases which give out bad smells and comprise various kinds of components such as acidic, basic, oxidizing and/or reducing ones as well as the foregoing contaminants in the form of aerosols. Moreover, the rate of reaction observed for the reaction of an aqueous ammonia solution with a dilute sulfuric acid solution is 100%, but it has been found that the rate of cleaning achieved is frequently not more than 50%, even when the dilute sulfuric acid solution is brought into contact with ammonia gas in a conventional scrubber. In addition, such a cleaning device and the technique for the operation thereof have not yet been established.

(10) Method for Sprinkling, in Exhaust Duct, an Aqueous Solution of Low Molecular Weight Cleaning Agent: Even when sprinkling, in an exhaust duct, the same aqueous solution used in the foregoing item (9), it was frequently observed that the gas-liquid contact rate achieved by the treatment was insufficient or considerably low and that the crystals formed through the reaction were deposited on the interior of the duct to thus make the passage of the gas flow difficult. In this case, the aerosol does not have kinematic characteristics like those observed for the gas, the probability of the collision thereof with sprayed mist was considerably low and good results were obtained only in a low frequency.

(11) Washing Type Cleaning Agent for Washing the Contaminated Surface of an Object and Cleaning Method Using the Same: Since various kinds of contaminants are adhered to and stuck fast to the surface, the surface is occasionally or periodically cleansed through wiping or washing, using the following agents and/or the following cleaning methods:

A) Cleaning of Air-Conditioning System (hereunder referred to as air-conditioner): In most of cases, the air-conditioner is contaminated with lamp soot, oil films, nicotine or tar derived from tobacco, mold (fungi), bacteria, mites and the dead bodies thereof, dust, substances emitting composite bad smells such as substances attributable to the evil body smells and harmful aerosols, which are deposited on or adhered to the aluminum heat exchanger and the regions surrounding the same, these contaminants are, as a result, released into the interior of the room where the air-conditioner is installed, this accordingly reduce the rate of heat exchange of the air-conditioner and the latter wastefully consumes an excess electric power. The business of periodically washing such an air-conditioner has recently widely been popularized and one of the methods for cleaning the same, which have now been favorably noticed, comprises the steps of covering the air-conditioner with a plastic bag while protecting the electric circuits thereof including the distributing wires from coming into contact with any cleaning liquid and preventing any leakage of the cleaning liquid in the conditioner; and then injecting, under pressure, three kinds of cleaning liquids, in order, through the opening of the cover to thus cleanse the air-conditioner. In this respect, a dilute aqueous solution of caustic soda is used as the first cleaning liquid, a dilute aqueous solution of phosphoric acid is used as the second cleaning liquid, and water is used as the third cleaning liquid.

However, the method applied to the cleaning of the air-conditioner never permits the cleaning of the heat exchangers used in, for instance, Chinese restaurants and restaurants serving foreign dishes since the foregoing contaminants and firm oil films (hereunder referred to as oil stains) are formed on the heat exchangers used therein.

B) Cleaning of Filters of Large-Scale Air-Conditioner for Commercial Use: Filters prepared from fabrics or non-woven fabrics of polyester fibers are regularly replaced with new ones and the contaminated or used ones have conventionally been discarded in most of cases.

However, the regulations concerning the waste matter have recently been strengthened and accordingly, it has been necessary to repeatedly wash and reuse these materials. The widely used method for cleaning these materials comprises the steps of washing them with an aqueous solution of a hydroxide or carbonate of sodium or potassium, which corresponds to a deleterious substance or a poison, which has a high pH value and to which a surfactant is further incorporated; and then washing with water. However, the method is still insufficient since it may incompletely remove lamp soot, hardened oils and fats, mycelia of fungi, and the smells of tobacco, and this method still suffers from various problems in that the filter thus cleansed still gives out bad smells, that it has a blackish appearance due to the recontamination with lamp soot and dust, even after water-washing, that the polyester fibers are dissolved because of the washing with a strongly alkaline cleaning liquid and that the method additionally requires the post-treatments such as the neutralization of the waste liquor prior to the discharge thereof and a treatment thereof for the prevention of any foaming in the river after the discharge thereof.

C) Cleaning of Various Kinds of Textile Goods: There have been used, for the cleaning of these goods, a variety of powdery and liquid detergents, each of which comprises, for instance, enzymes, oxidizing agents such as sodium percarbonate, builders, surfactants and other auxiliary agents. These usually used detergents have not yet solved such a problem of the complete removal of intensive bad smells emitted from common clothes commercially cleansed, household diapers and clothes and those used in the care facilities, during ironing out thereof after cleansing, rinsing with water and centrifugal dehydration and/or during the storage of the finished such goods, as well as the complete removal of, for instance, the offensive smells of the armpit adhered to, for instance, shirts, trousers and undershirts and yellowish spots or stains formed on light-colored trousers and undershirts due to the urine.

D) Elimination of Contaminants from the Atmosphere in the Interior of Rooms: There have gradually been emitted, in the interior of rooms, various kinds of contaminants, in the form of gases, detailed above, which are adsorbed on and adhered to the surface of, for instance, wallpaper, wooden wallpaper, decorated plywood, wooden partition wall materials, tatami mats, glass doors and windows, used in houses, office rooms, eating houses, stores, sleeping accommodations or the like, as well as the surface of floor boards, ceiling boards, cooking rooms, cooking tables, bath rooms or the like; further VOC and/or SPM originated from insecticides for tatami mat, those for killing white ants, sprinkled under the floor, paints and varnishes during drying may spread throughout the interior of the rooms and the residents may accordingly be attacked with sick-house syndromes. Moreover, there has not yet been developed any cleaning liquid which can completely recover the beautiful appearance of the ventilating fans and the interior materials provided thereon with mixed oils and fats-derived contaminants, like the foregoing air-conditioner, by cleansing through wiping and therefore, it would be necessary to replace the air-conditioner and the interior materials per se with new ones. However, such replacement never permitted the complete removal of the bad smells fast stained on the interior of rooms.

E) Cleaning of Product-Manufacturing Line for Liquid Products: Beverages and liquid seasonings are packaged in containers such as metallic cans, glass bottles and waterproof paper containers in an automated line of an automated filling machine. However, a variety of goods should be produced, the kinds thereof should be changed from season to season, and the production lot of each good is often small as compared with the manufacturing and packaging capacity of the device. The production of these various kinds of goods are carried out using the same production line and therefore, the latter should frequently be cleansed. In this case, if a very small amount of the good previously produced still remains in the line even after the washing thereof and it is mixed with the subsequently produced good, the taste and texture as well as the flavor of the resulting good may be impaired and the commercial value of the resulting good is in turn considerably reduced. To remove such residues present in the line in a very small amount, the line should be washed under severe conditions. In a typical example, the washing requires the use of 6 steps and the use of tap water in an amount of 6 times the volume of the good produced using the line and further the washing step requires the amount of heat to be used for heating the tap water for washing to a temperature ranging from 85 to 90° C. and it is said that it takes 3 hours for the completion of each washing step.

However, the goods such as juices of apple and peach and seasonings containing slurry-like citrus fruits have the smells peculiar thereto, whose removal is quite difficult and, in most of case, the same step is repeated not less than three times for the complete removal thereof. Therefore, it has been desired for the development of a cleaning agent and a cleaning method, which certainly permit the deodorization by a single cleaning step.

F) In factories for manufacturing electronic substrates, for repairing motorcars and machines, and those for dry-cleaning, there have still been used, for instance, a hydrocarbon-based solvent including gasoline quite susceptible of ignition, caustic soda and an aqueous detergent containing surfactants in order to remove fats and oils, and petroleum-derived hydrophilic and hydrophobic contaminants from various products, parts, clothes or the like, but there has thus been desired for the development of an aqueous detergent which has a low BOD and/or a low COD and which is highly safe.

(12) Mask for Preventing Virus-Infection: In the pandemic stage of viral infectious diseases, it has been said that the wearing of masks for the prevention of the infiltration of any virus is quite effective for the commutation passengers, passengers, and peoples who go out, but there has not yet been developed any mask which has high quality like the anti-gas masks for the military and industrial use, which is light weight like the usual cotton gauze mask and which is quite easy for wearing.

(13) Prior Arts:

There has been proposed a technique for the removal of gaseous and aerosol-like contaminants, which comprises the step of sprinkling, into the atmosphere, a dilute aqueous solution containing an amphoteric and alkanol-amine and a neutralized anionic polyacrylamide (see, for instance, Patent Documents 1 to 3 specified below).

In addition, there has likewise been proposed a technique concerning a detergent, comprising, as essential components, organic and/or inorganic cleaning agents and a high molecular weight compound which is a copolymer of a derivative of acrylamide and other monomers, having either anionic, cationic or amphoteric characteristics, whose aqueous solution shows cohesive properties and which has a molecular weight of not less than 1,000,000 (see, for instance, Patent Document 4 specified below). According to this technique, it is said that the dilute aqueous solution thereof can certainly prevent any re-contamination of the object to be washed such as fibrous materials with inorganic fine particulate contaminants such as the lamp soot and dust such as soils originated from the rinsing step of the object obtained after cleaning of the same and the dilute aqueous solution likewise permits the removal of any polymerized oily contaminants attached to the fibrous materials.

Moreover, there has also been proposed a gas-cleaning technique which makes use of a detergent showing the chemical reactivity with gaseous contaminants of 100% and a scrubber provided with a built-in paper-based filler material (see, for instance, Patent Documents 5 and 6 specified below). According to this technique, it is said that the rate of cleaning would be 100%, if the operational conditions are so controlled that the gas-liquid contact rate of the scrubber becomes 100%.

Patent Document 1: The specification of Japanese Patent No. 2,132,366;

Patent Document 2: The specification of Japanese Patent No. 2,134,708;

Patent Document 3: The specification of Japanese Patent No. 2,775,162;

Patent Document 4: The specification of Japanese Un-Examined Patent Publication Hei 7-216389;
Patent Document 5: The specification of Japanese Un-Examined Patent Publication 2001-149739;
Patent Document 6: The specification of Japanese Un-Examined Patent Publication 2004-313893.

SUMMARY OF THE INVENTION

Problems That the Invention is to Solve

However, the foregoing techniques (1) to (13) still suffer from the following problems. In addition, the techniques disclosed in the foregoing prior arts would permit the removal of gaseous contaminants to some extent, but the fact is that the extent of the cleaning rate is still low.

Accordingly, it is an object of the present invention to solve the following problems. In this respect, the conventional cleaning agents have been ineffective for the solution of these problems or the cleaning effects thereof have been insufficient:

In other words, (A) it is an object of the present invention to remove contaminants or eliminate any bad smell of various contaminated materials. More specifically, the newly developed cleaning agent of the present invention can be sprayed onto or sprinkled into contaminants such as VOC in the spaces, insecticides, miticides or tickicides, incense sticks and formaldehyde; suspending fine dust such as powders, house dust, sand dust and spores of fungi; smells peculiar to raw waste, perfumes, incense sticks, spices, smells of the armpit, garlic, and fungi; suspending or floating bacteria, foamy bacteria, eumycetes (fungi), spores thereof and viruses; the smells peculiar to fires, the smells derived when thermally decomposing oil films, and the smells peculiar to timbers, rubber, asphalt, and plastics; contaminants present in spaces, for instance, virulently poisonous neurotoxic gases such as sarin, tabun, soman, phosgene and VX gas. In this connection, the cleaning agent thus traps them through the chemical inclusion effect thereof to increase the particle size of the inclusion materials and to precipitate them. Simultaneously, the cleaning agent can undergo, within the particles, chemical reactions with them to thus detoxify the same.

(B) It is another object of the present invention to remove contaminants or eliminate any bad smell of various contaminated materials. More specifically, the newly developed cleaning agent of the present invention can be sprayed on the surface of objects which are contaminated with contaminants present in the atmosphere through adhesion to or adsorption on the same; it is sprayed, in the form of a liquid, on the entire internal surface of a room which are contaminated with contaminants adhered thereto in the form of fine particulate dust; it is used for wiping clothes for the removal of bad smells remaining thereon in place of the dry-cleaning of the clothes; and further it is sprayed onto the surface of various objects to remove bad smells and to prevent the proliferation of mold. Subsequently, the objects may be subjected to optional treatments such as the brushing and the application of ultrasonics to thus further cleanse the surface thereof.

(C) It is a further object of the present invention to remove contaminants or eliminate any bad smell of various contaminated materials. More specifically, the newly developed cleaning agent of the present invention can be sprayed on the surface of various objects, to which visible contaminants are adhered, for instance, the interiors of buildings such as the internal surface of a smoking room, the interior of ill-kept second-hand houses, the interior of Chinese restaurants and fried food shops, and the interior of the aquatic product-manufacturing factories; contaminated metallic and plastic surface subjected to, for instance, the cutting, extrusion molding and forging processes in machine-producing and repairing factories in which process oils such as cutting oil are used; and contaminated soft goods or textile materials, to thus remove the contaminants and to make them clean.

(D) It is a still further object of the present invention to remove contaminants or eliminate any bad smell of various contaminated materials. More specifically, the newly developed cleaning agent of the present invention can be sprinkled in the contaminated atmosphere containing VOC in a high concentration to thus trap, coagulate and remove the VOC.

(E) It is a still another object of the present invention to remove contaminants or eliminate any bad smell of various contaminated materials. More specifically, the newly developed cleaning agent of the present invention can, directly or indirectly through a duct, be sprayed on or sprinkled in the atmosphere of, for instance, the atmosphere of compost-making factories in which waste foods are used as the starting materials, poultry farms and raw rubber-processing factories; biogases derived from cattle droppings and wooden waste materials; aerosol-like contaminated substances such as a mixed exhaust gases containing fine dust and tar-like contaminants; and multi-component exhaust gases containing various molecular contaminants, to thus deodorize and cleanse these materials.

(F) It is a still another object of the present invention to remove contaminants or eliminate any bad smell of various contaminated materials. More specifically, the newly developed cleaning agent of the present invention can be used for certainly deodorizing, for instance, the goods such as juices of apple and peach and seasonings containing slurry-like citrus fruits, which have the smells peculiar thereto and emitted from, for instance, food factories.

(G) It is a still another object of the present invention to provide a simple mask used for the prevention of any bacterial and viral infection. More specifically, the wearing of such a mask would make the breath of wearers clean.

Means for the Solution of the Problems

The inventors of this invention have variously investigate the foregoing objects of the invention, have found that the foregoing problems can be solved by the use of a composition as a cleaning agent, which comprises an aqueous solution of aqueous dispersion containing a poly(meth)acrylamide having a specific average molecular weight; a specific bactericidal or antibacterial agent; and a solvent such as monopropylene glycol, dipropylene glycol or tripropylene glycol and have thus completed the present invention.

In other words, according to the present invention, there is provided a cleaning agent which comprises (A) an aqueous solution or an aqueous dispersion containing a linear poly(meth)acrylamide having an average molecular weight of not less than $5 \times 10^6$ as determined according to the intrinsic viscosity-determining technique in a concentration ranging from 0.0001 to 0.01% by mass; (B) a poly(hexamethylene-biguanide) hydrochloride represented by the following general formula (1); and (C) at least one compound selected from the group consisting of propylene glycol, dipropylene glycol, tripropylene glycol, diethylene glycol, triethylene glycol, tetraethylene glycol, and ethers of ethylene glycol and propylene glycol with alcohols each having 1 to 3 carbon atoms, and esters thereof with fatty acids each having 1 to 3 carbon atoms, glycine and taurine:

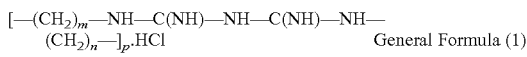

General Formula (1)

wherein m and n each represent an integer ranging from 2 to 5 and p is an integer ranging from 5 to 16.

Effects of the Invention

The use of the cleaning agent according to the present invention permits the achievement of the following effects (1) to (5):
(1) The cleaning agent can capture contaminants suspended in a gas and can immediately settle down the same to thus make the gas clean.
(2) Contaminants can be settled down by sprinkling the cleaning agent into a gas flow containing the contaminants within a duct to thus make the gas flow clean.
(3) The cleaning agent is sprayed onto the surface of an object carrying substances emitting bad smells and/or harmful gases and contaminants such as dirt, spots or stains, which are adhered to the surface, optionally followed by rubbing with a cleaning and wiping member and washing the surface by applying a jet of water under pressure to thus make the object's surface clean.
(4) The cleaning agent is incorporated into a liquid containing harmful substances and/or subjects emitting unpleasant smells to thus detoxify and deodorize the liquid.

DETAILED DESCRIPTION

The cleaning agent according to the present invention comprises (A) an aqueous solution or an aqueous dispersion containing a linear poly(meth)-acrylamide (hereunder referred to as "PAM") having an average molecular weight of not less than $5 \times 10^6$ as determined according to the intrinsic viscosity-determining technique.

The PMA contained in the cleaning agent of the present invention is one having an average molecular weight of not less than $5 \times 10^6$ as determined according to the intrinsic viscosity-determining technique. This would permit the uniform spraying of the surface of an object with the resulting cleaning agent.

If the average molecular weight of the PAM used in the present invention is not less than $5 \times 10^6$ in terms of the value determined according to the intrinsic viscosity-determining technique, the PAM is strongly conjugated with other essential components of the cleaning agent and the resulting agent has a high ability of forming a water-retentive gel and can maintain the intended effects of the present invention, i.e., cleaning effects such as bactericidal and deodorization effects over a long period of time. While if the average molecular weight of the PAM is less than $5 \times 10^6$, the resulting cleaning agent shows insufficient cohesion and accordingly, the intended functions of the agent and the durability thereof are lowered. For this reason, the average molecular weight of the PAM is preferably not less than $1.5 \times 10^7$. In this respect, however, the polymers having an average molecular weight of less than $5 \times 10^6$ may be used in the agent of the present invention by incorporating them into those having an average molecular weight of not less than $1.0 \times 10^7$ in a low rate.

The PMA used in the present invention exists in the form of an aqueous solution of an aqueous dispersion and accordingly, a part thereof may be dispersed in an aqueous solution or a part thereof may be dissolved in an aqueous dispersion.

The PMA is used in the agent of the present invention as an aqueous solution or an aqueous dispersion having a concentration ranging from 0.0001 to 0.01% by mass. This is because if the concentration thereof is less than 0.0001% by mass, the resulting cleaning agent cannot show the intended effect of the poly(meth)-acrylamide, while if the concentration thereof exceeds 0.01% by mass, the viscosity of the resulting cleaning agent is too high to form fine mist thereof.

Moreover, when using the aqueous solution or aqueous dispersion of PAM in the applications which are accompanied by the formation of gel, for instance, the cleaning of the foregoing contaminated gas, the precipitation of suspended very fine dust, the cleaning of contaminated objects and masks, it is preferred to increase the solid content of the cleaning agent through drying of the same to thus improve the ability thereof to form a water-retentive gel.

In addition, the PAM used in the present invention is preferably an amphoteric charged polymer carrying both anionic and cationic groups in the molecule. When spraying the cleaning agent, the water and solvent are evaporated from the resulting mist thereof, the anionic and cationic groups come in close contact with one another to thus form bridges or crosslink through the intramolecular salt-formation, the cleaning agent is thus converted into a water-insoluble and water-swelling gel, the resulting gel can undergo the inclusion of the bactericidal and antibacterial agent in the cleaning agent to thus form microcapsules and therefore, the cleaning agent shows bactericidal and antibacterial characteristics and the deodorization properties and can ensure the longer durability of such effects.

Examples of the foregoing anionic groups usable herein are carboxyl groups, sulfonate groups, sulfo-alkyl groups, phosphate groups, phosphonate groups and alkaline metal salts thereof. In addition, the cationic groups usable herein include, for instance, those derived from quaternary ammonium salts, dialkyl-aminoalkyl groups, aminomethyl-acrylamide groups, and vinyl-imidazoline groups. Preferably used in the present invention include polymers in which the sum of these anionic and cationic groups, for instance, falls within the range of from 30 to 70% by mole and the ratio of anionic groups to cationic groups is approximately 1, because of their multifunctional properties. The PAM used in the present invention further comprises, in the molecule, additional functional groups such as other nonionic amido groups and imido groups.

Such a PAM can be prepared by the radical-polymerization of a monomer carrying the foregoing functional groups and an ethylenically unsaturated bond, in water.

[Examples of Monomers Carrying Anionic Groups]
1) Monomers Carrying Carboxyl Groups: Acrylic acid, methacrylic acid, crotonic acid, 2-(meth)acryloyloxy-ethyl succinic acid, 2-(meth)acryloyloxy hydrophthalic acid, maleic acid, fumaric acid or monoalkyl esters thereof,
2) Monomers Carrying Sulfonate Groups, Sulfoalkyl Groups, Phosphate Groups or Phosphonate Groups: vinyl sulfonic acid, mono[2-(meth)acryloyloxy-ethyl] acid phosphate, sulfo-ethyl (meth)acrylate, sulfo-propyl methacrylate, 2-(meth)acryl-amide-2-methyl sulfonic acid, styrene sulfonic acid and vinyl sulfonic acid;

[Examples Carrying Cationic Groups]
3) Monomers Carrying Dialkyl-aminoalkyl Groups, Aminomethyl-acrylamide Groups, or Vinyl-imidazoline Groups: Dimethyl-aminoethyl (meth)acrylate, diethyl-aminoethyl (meth)acrylate, dimethyl-aminopropyl (meth)acrylate, diallyldimethyl-amine, diallyldiethyl-amine, and vinylbenzyl-methylamine;

4) Monomers Having Structures of Quaternary Ammonium Salts: Monomers each having a structure of quaternary ammonium salt obtained by acting, on the monomers carrying cationic groups listed above in connection with item-3), at least one inorganic or organic acid selected from the group consisting of hydrochloric acid, sulfuric acid, phosphoric acid, succinic acid, malonic acid, DL-malic acid, ascorbic acid, gluconic acid boride, galacto-gluconic acid, gluconic acid, citric acid, isovaleric acid, lactic acid, phosphorylated lactic acid, levulinic acid, propionic acid, and other acids. Specific examples thereof include 2-(meth)acryloyloxyethyl-trimethyl ammonium chloride, 2-hydroxy-3-(meth)acryloyloxypropyl-trimethyl ammonium chloride, diallyldimethyl ammonium chloride, vinylbenzyl-trimethyl ammonium chloride, or sulfides thereof.

In addition, it is preferred in the present invention to incorporate, into the PAM molecule, 2 to 10% (by mass) of specific hydrophobic groups in order to impart, to the resulting polymer, an ability of adsorbing oily contaminants. As such hydrophobic groups, there may be listed, for instance, alkyl groups, aralkyl groups, fluoroalkyl groups and dialkylsilyl groups, each having 4 to 18 carbon atoms; and siloxane groups each having 4 to 16 carbon atoms. The present invention uses such a polymer carrying at least one of these functional groups. In this respect, the polymer preferably comprises these hydrophobic groups in an amount ranging from 2 to 10% by mass. The polymer would show the foregoing intended effects if the polymer used comprises the hydrophobic group in an amount specified above.

Examples of the methods for the introduction of such hydrophobic groups into the foregoing polymer include 1) a method comprising the step of copolymerizing the raw monomer of the polymer with a (meth)acrylic acid ester carrying, for instance, a hydrophobic alkyl group having 4 to 18 carbon atoms in its ester group, as a comonomer; 2) a method comprising the steps of reacting the amido group of a poly(meth)acrylamide with an aldehyde to thus form a hydroxymethyl derivative, subsequently introducing an alkyl group into the derivative through the reaction thereof with an amine and/or an alcohol (Mannich reaction) or reacting the amide-amino groups of a poly(meth)acrylamide with the ketone groups of a copolymer into which diacetone groups are introduced; 3) a method comprising the steps of introducing carboxyl groups into the polymer molecules through the copolymerization like that described above in connection with the item 1) or through the hydrolyzation of the amide groups thereof and then converting the carboxyl groups into esters or amides. The monomers carrying hydrophobic groups and used in these methods are selected from those having, in the molecule, 1 to 3 functional groups such as alcohol-derived groups, amine-derived groups or double bonds.

The aqueous solution or the aqueous dispersion of PAM, used in the present invention preferably comprises a water-soluble acrylic copolymer. Such a water-soluble acrylic copolymer is one obtained by copolymerizing a copolymerizable monomer carrying an anionic group such as a carboxyl group or a sulfonate group with another copolymerizable monomer and then neutralizing the resulting copolymer with ammonia, an amine, an alkanolamine, or sodium hydroxide to thus make the copolymer water-soluble. Examples of copolymerizable monomers each carrying a carboxyl group and monomers each carrying a sulfonate group include those having anionic groups as has been described above. In addition, examples of other copolymerizable monomers are aliphatic conjugated dienes such as 1,2-butadiene, 1,3-butadiene, isoprene, and chloroprene; ethylenically unsaturated aromatic monomers such as styrene, α-methylstyrene, vinyl toluene, and chloro-styrene; ethylenically unsaturated nitriles such as acrylonitrile, and methacrylo-nitrile; vinyl esters such as vinyl acetate, and vinyl propionate; halogenated vinylidenes such as vinylidene chloride, and vinylidene bromide; and (meth)acrylic acid esters.

The water-soluble acrylic copolymers used in the present invention are preferably ammonium salts of (meth)acrylic acid/(meth)acrylic acid ester copolymers, among others. In this respect, examples of such (meth)acrylic acid esters are methyl (meth)acrylates, ethyl (meth)acrylates, propyl (meth)acrylates, butyl (meth)acrylates, amyl (meth)acrylates, hexyl (meth)acrylates and cyclohexyl (meth)acrylates Moreover, the weight average molecular weight of the water-soluble acrylic copolymer is preferably not less than 10,000.

The cleaning agent of the present invention can efficiently cover contaminant-containing gelled particles since the agent comprises this water-soluble acrylic copolymer incorporated therein. More specifically, the cleaning agent once captures and traps such contaminants therein to thereby prevent any secondary release of the contaminants once trapped. In particular, it is quite preferred that an aqueous solution of such a water-soluble acrylic copolymer is sprinkled into a duct after sprinkling a mixture of the present invention comprising (A) an aqueous solution or dispersion of a poly(meth)acrylamide; (B) a poly(polymethylene-biguanide) hydrochloride; and a compound (C) into the duct. This is because the cleaning agent can show the intended effect of the invention at the highest possible level.

In addition, the aqueous solution or dispersion of PAM used in the present invention preferably comprises a water-soluble inorganic salt. Examples of such water-soluble inorganic salts are common salt; alkali metal salts of sulfuric acid such as sodium sulfate and potassium sulfate; alkali metal salts of nitric acid such as sodium nitrate, potassium nitrate, calcium nitrate and zinc nitrate; salts of sulfur oxides; and calcium chloride.

The molecular conformation of the PAM as an ionic polymer is controlled in such a manner that the interaction between the neighboring ionic groups is limited to the lowest possible level, but the ionic dissociation thereof is dependent on the ionic concentration in the surrounding environment and the ionic groups present in the polymeric compound have a reduced degree of dissociation proportional to the ionic concentration, and the ionic groups on the polymeric molecule are present as ionic pairs. Therefore, the interaction between the neighboring ionic groups is reduced to a lower level, this accordingly, makes the intramolecular formation of gel-like aggregates easy and the ionic concentration in the aqueous solution can thus be increased.

As has been described above, the PAM used in the present invention is preferably a charged amphoteric PAM, but it is preferred to use the PAM in combination with the foregoing gelling agent for the further enhancement of the gel-forming ability of the resulting cleaning agent.

Examples of such gelling agents include water-soluble alkali metal salts; water-soluble divalent alkaline earth metal salts such as magnesium nitrate; aluminum compounds; dibasic carboxylic acids having 2 to 18 carbon atoms and ammonium salts, amine salts and amino-alcohol salts thereof; dihydrazides of water-soluble high molecular weight compounds such as succinic acid dihydrazide, adipic acid dihydrazide, and dodecane dihydrazide; and glytaraldehyde and glyoxal. Moreover, also usable herein include (meth)acrylamides having charges opposite to those of the foregoing poly(meth)acrylamide in an aqueous solution. It is preferred to use, in the form of an aqueous solution, at least one of these gelling agents in an amount ranging from 1 to 100% by mass relative to the solid content of the PAM aqueous solution and the gelling agent is most preferably added to the cleaning agent in an amount ranging from 20 to 80% by mass relative to the solid content.

Moreover, the gelling agent may be added to the aqueous solution or dispersion of PAM, but the gelling agent and the aqueous solution or dispersion can be used separately. For instance, the aqueous solution or dispersion of PAM is first sprayed on a contaminated object and then the object is sprayed with the gelling agent.

Specific examples (i) to (vii) of the aqueous solution or dispersion of PAM will now be detailed below:

(i) An aqueous solution or dispersion containing an anionically charged copolymer of a (meth)acrylamide and a compound having, in the molecule, a carboxyl group and/or sulfonate group and an ethylenically unsaturated double bond and a gelling agent;

(ii) An aqueous solution or dispersion of an anionically charged polymer, prepared by hydrolyzing, in water, the amido groups present in a poly(meth)acrylamide polymer or copolymer containing (meth)acrylamide units as an essential constituent and then adding a gelling agent to the solution or dispersion;

(iii) An aqueous solution or dispersion of a charged amphoteric poly(meth)-acrylamide, prepared by converting 10 to 90% by mole of the amide groups in the poly(meth)acrylamide polymer or copolymer specified above in the foregoing items (i) and/or (ii) into the methylol thereof, and further reacting the resulting methylol derivative with at least one member selected from the group consisting of amines mono- to tri-substituted with members selected from alkyl groups having 1 to 4 carbon atoms, alcohol-derived groups having 1 to 4 carbon atoms, cyclopentyl group and/or cyclohexyl group; N-vinyl-2-pyrrolidone, 2-pipecoline, 3-pipecoline, 4-pipecoline, homo-piperazine, N-methyl-piperazine, 2-methyl-piperazine, piperidine, pyrazine, morpholine and derivatives thereof having 1 to 3 alkyl substituents, in an amount of not less than the equivalent corresponding to the methylol-conversion rate, to thus introduce cationic groups into the polymer, or the foregoing aqueous solution or dispersion to which at least one gelling agent is further added;

(iv) An aqueous solution or dispersion of a charged amphoteric terpolymer which is prepared by copolymerizing (meth)acrylamide, a monomer having, in the molecule, a carboxyl group and/or sulfonate group and an ethylenically unsaturated double bond and a monomer having, in the molecule, a cationic group and an ethylenically unsaturated double bond, in a gas stream of an inert gas injected into the reaction system, which is free of any oxygen, in the presence of a peroxide; or the foregoing aqueous solution or dispersion of such a charged amphoteric terpolymer, to which at least one gelling agent is further added;

(v) An aqueous solution or dispersion of a polymer prepared by reacting (meth)acrylamide with a monomer having, in the molecule, a cationic group and an ethylenically unsaturated double bond to thus introduce cationic groups into the same; or the foregoing aqueous solution or dispersion of such a positively charged polymer, to which at least one gelling agent is further added;

(vi) An aqueous solution or dispersion which comprises an aqueous solution or dispersion of positively charged polymer and/or copolymer prepared by introducing positively charged groups into a nonionic polymer or copolymer composed of (meth)acrylamide as an essential constituent; and at least one gelling agent incorporated therein;

(vii) An aqueous solution or dispersion obtained by solution-polymerizing a mixture comprising not more than 50% by mole of a monomer having a carboxyl group and another copolymerizable monomer in a peroxide-containing water, aqueous ammonia or ethyl alcohol while blowing an inert gas into the reaction system; removing the unreacted monomers and the ethyl alcohol through the steam distillation under reduced pressure to thus give a water-soluble polymer; and further blending the resulting water-soluble polymer, to which aqueous ammonia is added, with not more than 50% by weight (in terms of the solid content) each of the foregoing aqueous solutions or dispersions (i) to (v), or the foregoing aqueous solution or dispersion to which at least one gelling agent is further added.

The cleaning agent of the present invention comprises a poly(polymethylene-biguanide) hydrochloride (hereunder referred to as "PHMB") represented by the following general formula (1), as a bactericidal and antibacterial component (B):

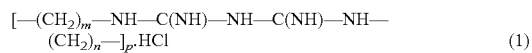

$$[-(CH_2)_m-NH-C(NH)-NH-C(NH)-NH-(CH_2)_n-]_p \cdot HCl \qquad (1)$$

wherein m and n each represent an integer ranging from 2 to 5 and p is an integer ranging from 5 to 16.

The PHMB used in the present invention as the component (B) comprises 5 to 16 repeating units given in the brackets, but the number of the foregoing repeating units present in the PHMB preferably ranges from 8 to 13 and more preferably 12.

In addition, it is preferred in the present invention to use a poly(hexa-methylene-biguanide) hydrochloride represented by the general formula (1) wherein m and n each represent 3.

In this connection, if the number of the foregoing repeating units present in the component (B) falls within the range specified above, the resulting cleaning agent shows intensive efficacy against wide variety of microorganisms, and the agent is non-volatile, has a low toxicity and is excellent in the heat stability.

Specific examples of the PHMB represented by the general formula (1) used as the component (B) include "Proxel 1B" available from ARCHI CHEMICAL Japan Co., Ltd.).

The PHMB used in the present invention as the component (B) is incorporated into the cleaning agent of the invention in an amount ranging from 0.0001 to 1% by mass of the cleaning agent and preferably 0.0001 to 0.1% by mass.

Moreover, it is also possible to use a compound other than the PHMB used in the present invention, as the bactericidal, antibacterial, antifungal and/or bacteriostatic agents.

The cleaning agent of the invention comprises, as a solvent, (C) at least one compound selected from the group consisting of propylene glycol, dipropylene glycol, tripropylene glycol, diethylene glycol, triethylene glycol, tetraethylene glycol, and ethers of ethylene glycol and propylene glycol with alcohols each having 1 to 3 carbon atoms, and esters thereof with fatty acids each having 1 to 3 carbon atoms, glycine and taurine. Among these solvents, preferably used herein include, for instance, propylene glycol, dipropylene glycol, tripropylene glycol and glycine since they have an excellent ability of solubilizing the foregoing PHMB as the component (B) and they can effectively show their bactericidal and antibacterial and deodorizing characteristics and most preferably used herein include, for instance, dipropylene glycol, tripropylene glycol and glycine.

When bringing the foregoing to a conclusion, the cleaning agent according to the present invention is an aqueous solution of amphoterically charged PAM having an average molecular weight of not less than $1.5 \times 10^7$ and preferably around $2.0\times10^7$ as determined according to the intrinsic viscosity technique and the aqueous solution of the PAM is characterized in that it can maintain the complete water-solubility when practically using the same, but it can penetrate into, for instance, a substance giving out bad smells to thus increase the concentration thereof and that it can immediately form firm water-retentive gels due to the increase in the concentration to thus enclose the substance in the resulting gels.

The cleaning agent of the present invention can likewise be used for the removal of the contaminants adsorbed on the surface of an object. In this case, the agent preferably comprises a fatty acid salt and/or a derivative thereof.

Such a fatty acid salt and/or a derivative thereof are preferably in the form of a water-soluble, water-dispersible or emulsifiable formulation, in other words, in the form of an aqueous preparation and the amount thereof to be used preferably ranges from about 0.1 to 5% by mass on the basis of the total mass of the aqueous solution or dispersion of PAM.

The foregoing fatty acid salt is preferably a fatty acid salt, which has 12 to 24 carbon atoms and at most one double bond, which is non-dryable and which sparingly gives out a bad smell and, in particular, the fatty acid salt is preferably one having 16 to 18 carbon atoms. Examples of fatty acids each having 16 to 18 carbon atoms include palmitic acid, palmitoleic acid, stearic acid and oleic acid. Examples of the salts of these fatty acids are amine salts, sodium salts and potassium salts. Among these salts, preferred are amine salts. More particularly, specific examples thereof preferably used herein include mono-isopropanolamine salts, di-isopropanol-amine salts and tri-isopropanolamine salts. The amine salts are excellent in the ability of penetrating into contaminants. In addition, metallic salts are excellent as the lubricants and therefore, it would be most preferred to use these amine salts and an alkali metal salt in combination. Specific examples of these amine salts and metal salts are amine soap, and metallic soap.

Moreover, it has been known that the surfactant can control the conformation of a high molecular weight compound and accordingly, it is preferred to additionally incorporate a surfactant into the cleaning agent of the present invention.

Preferably, the cleaning agent of the present invention further comprises a phase transfer catalyst. This phase transfer catalyst herein used means any catalyst which can transfer between two phases to thus promote a desired reaction and specific examples thereof include quaternary ammonium salts, quaternary phosphonium salts, glycol ethers and crown ethers. Among them, preferably used herein are quaternary ammonium salts, glycol ethers and crown ethers. The use of these phase transfer catalysts would permit the improvement of the configuration level of the non-uniform electrons to thus capture bad smells and contaminants and to make clear the contaminated air or atmosphere and contaminated substances.

Moreover, the cleaning agent of the present invention preferably comprises an alcoholamine. Examples of such alcoholamines include ethanolamine, isopropanolamine, butanolamine, (diethylamino)ethanol, N,N-dimethylethanol-amine, N-(2-aminoethyl)ethanolamine, N-methyl-diethanolamine, N,N-dibutyl-ethanolamine, N-methyl-ethanolamine, methyl 3-aminocrotonate, and 3-amino-1-propanol. These compounds have high wettability and accordingly, they can adhere even to faces to which the PAM is never adhered. They possess ion pairs and have a high penetrating power and therefore, they can penetrate into contaminated boundaries and sandwich the contaminants and bad smell-emitting substance between the ion pairs to thus make the contaminated substances clean.

Further, the cleaning agent of the present invention is preferably one comprising a magnetic substance in order to adsorb contaminants in the air on the same.

Examples of such magnetic substances preferably used herein are fine powdery iron, cobalt, nickel and magnetite, and magnetic fluids in which these metallic materials are dispersed by the aid of a surfactant.

The following are the description of the methods for cleansing, for instance, contaminated gases, contaminated substances and contaminated liquids, while making use of the foregoing cleaning agent.

[Method for Cleansing Contaminated Gases]

According to this method, a contaminated gas can be cleansed by sprinkling the foregoing cleaning agent in a gas containing contaminants to thus trap and precipitate the contaminants.

Examples of the contaminants included in the foregoing contaminant-containing gas are gaseous substance giving out a bad smell, harmful gases, aromatic substances, fine particulate dust, fume, mist, tar, harmful microorganisms, spores, and viruses.

The method for cleansing a contaminated gas using the foregoing cleaning agent will now be described in more detail below. For instance, a contaminated gas comprises, in the suspended conditions, a gaseous substance giving out a bad smell, harmful gases, aromatic substances, fine particulate dust, fume, mist, tar, harmful microorganisms, spores, and viruses, as well as contaminants comprising mixture thereof in their molecular states and in the form of aerosols.

Specific cleaning methods will be detailed below.

1) A contaminated gas is confined in a closed or semi-closed space, the cleaning agent is sprinkled in the space in its fine particulate state using a sprayer to collectively trap the suspended contaminants while making use of the inclusion action of the agent, to thus convert them into coarse particles and to thereby settle them. Thereafter, the resulting adhesive precipitates, whose ability of undergoing re-suspension due to the action of the wind is considerably reduced, can be removed by the use of a vacuum cleaner or a broom or a dustcloth.

2) A gas containing suspended contaminants is introduced into a tank or a sprayer type scrubber which has a volume capable of reducing the flow rate of the gas and which is connected to an exhaust duct, in turn, communicated to an air blower, then the cleaning agent of the present invention is sprinkled into the tank or the scrubber to thus trap the contaminants and to convert them into coarse particles and then the exhaust liquid settled down to the bottom and then solidified was discharged to the exterior of the apparatus, or simultaneously or separately, the cleaning agent of the present invention is used in the scrubber in the form of a liquid to trap the contaminants and the exhaust liquid settled down to the bottom and solidified was discharged to the exterior of the apparatus. In this case, it is preferred to carry out the scrubber cleaning step using the cleaning agent of the present invention as a cleaning liquid after the sprinkling of the cleaning agent in the scrubber, from the viewpoint of the cleaning efficiency.

The cleaning agent can continuously or intermittently be sprinkled in a contaminated gas using an ultrasonic vibratory sprayer. When the cleaning operation is carried out in a duct, the cleaning agent of the present invention is sprinkled into the same in a direction opposite to that of the gas flowing through the same till the gas is externally exhausted. Alternatively, when confining a gas containing suspended contaminants in an exhaust duct or a chimney installed and elongated in such a manner that the duct or chimney is downward inclined with respect to the perpendicular or horizontal direction, the cleaning agent of the present invention is sprinkled into the duct or the chimney.

Moreover, it is preferred that the aforementioned gelling agent is sprayed after spraying the cleaning agent of the present invention, and then the solidified contaminants or the liquid converted into liquid drops are removed. In addition, it is further preferred that the contaminated gas is brought into contact with a magnetic field generating device after the foregoing treatment with the cleaning agent and that the resulting solidified contaminants or the liquid converted into liquid drops are removed.

3) The cleaning agent of the present invention is sprinkled into the interior of a building having a height of not less than 2.5 m and containing suspended contaminants, in the form of very fine mist using an ultrasonic vibratory sprayer, while a horizontally rotatable propeller positioned above the mist-generating surface is operated to thus form an ascending air current so as to lift up the mist discharged from the sprayer even to a height exceeding the limit of the sprayer and to diffuse the same within the space in the building. Then the propeller is switched off to thus make the mist diffuse and drop in the space, the mist traps the suspended contaminants and converts them into coarse particles, while the mist undergoes diffusion and dropping. In this respect, the propeller is preferably intermittently operated in such a manner that it is again operated after the elapse of the time required for the dropping of the mist. The foregoing operations would permit the enclosure or inclusion of the contaminants within the mist.

The foregoing methods 1), 2) and 3) for cleansing contaminated gases are preferably carried out while adjusting the relative humidity of the contaminated gases to a level of not higher than 75%. The use of such condition would permit the substantial improvement of the contaminant-trapping rate of these methods.

According to the present invention, it is also possible to remove contaminants by introducing a gas containing suspended contaminants into a cleaning device provided with a layer comprising hygroscopic particles of paper and/or liquid-absorptive ceramic particles, which are impregnated with the cleaning agent of the present invention and a layer containing the cleaning agent of the present invention.

[Method for Cleansing Contaminated Objects]

This method is to make, clean, an object to which contaminants are adhered.

The cleaning agent is used for making, clean, the surface of a contaminated object such as those to which a mixed contaminants comprising hydrophobic gases and aerosols, in particular, hydrophobic contaminated objects which carry fats and oils, lamp soot, and greases adhered to, attached to, adsorbed on the same and/or oxidized, hardened and scorched products thereof stuck thereto and which further comprise soot, sand dust, metallic powders, microorganisms, insects and mites and the dead bodies thereof adhered to the objects in mixed states and which give out bad smells, unpleasant odors and emit harmful aerosol and whose appearance is severely impaired.

Specific methods for cleansing contaminated objects include, for instance, 1) a method comprising the step of rubbing the contaminated object with a cleaning and wiping material impregnated with a cleaning agent to thus remove the contaminants; 2) a method comprising the steps of spraying the surface of a contaminated object with a cleaning agent in the form of a quite fine mist and then drying the object; 3) a method comprising the steps of applying a jet of a cleaning agent under press to the surface of a contaminated object and thereafter optionally washing the object with water; 4) the method described in the item 3) in which the object is further dried after the water-washing step; 5) a method comprising the steps of immersing a textile good in a mixture of a detergent and a cleaning agent, applying a mechanical action onto the textile good, washing with water and dehydrating the same, and then ironing or drying the object thus cleansed; and a method comprising rubbing or wiping a textile good with a cleaning and wiping material containing a cleaning agent.

[Method for Cleaning Contaminated Liquid]

According to this method, a contaminated liquid is cleansed by adding the cleaning agent of the present invention to the contaminated liquid to thus trap the contaminants and to thereby remove the same.

[Other Methods Such as One for Cleaning the Breath Using Simple Mask]

This method can be applied to a simple mask for preventing bacterial and viral infection. More specifically, a woven or nonwoven fabric made of, for instance, cotton, rayon or vinylon is impregnated with the cleaning agent of the present invention and then dried and the resulting product is used as a dust-extracting cloth. This dust-extracting cloth is wetted with the water vapor present in the breath of a wearer and can thus form a water-insoluble and non-adhesive gel layer on the surface of the cloth to thus protect the wearer from the inhalation of any molecular and aerosol-like contaminants.

[Other Cleaning Methods]

Specific examples of the cleaning methods according to the present invention further include method for cleansing pipings and tanks included in a liquid food-packaging line in a food factory, which comprises the steps of stationarily cleansing the pipes and the tanks of the liquid food-packaging line after the packaging line is stopped, using a hot or cold aqueous solution containing the cleaning agent of the present invention to thus remove the residual components of the food still remaining in the pipings and the packaging tanks of the packaging line, and then further cleansing and sterilizing these pipings and tanks with a hot or cold aqueous solution containing the cleaning agent of the present invention over at least one time. The term "stationary cleaning" used herein means a system for safely and automatically washing a production installation according to simple operations without disassembling the installation. The foregoing method would permit the continuous production of a various kinds of refreshing beverages possessing smells peculiar thereto and strong taste, while using the lowest equipment investment and energy.

EXAMPLES

The present invention will hereunder be described in more specifically with reference to the following Examples. The term "%" used in the following Examples means "% by mass" unless otherwise specified.

[Cleaning of Asphalt-Containing Black Smoke Discharged Through Chimney]

Contaminated air is ejected from a variety of industrial companies and facilities through ducts, chimneys and deodorizing chimneys. According to the cleaning agent and cleaning method according to the present, invention, the cleaning agent of the present invention is sprinkled into the contaminated gas streams within such ducts, chimneys, deodorizing chimneys and the spraying chambers positioned between these members to thus make the molecular and/or aerosol-like contaminants present in the air settle down to the lower portions prior to the external discharge thereof, followed by the separation of the contaminants, subjecting the resulting waste liquor to the post-treatments to thus cleanse the gas streams and the subsequent exhaustion thereof. Accordingly, the cleaning agent of the present invention can certainly be used for the cleaning of the exhaust gases emitted from, for instance, a variety of production facilities, processing factories, or further hospitals, care facilities, public facilities and multistory buildings.

Reference Example 1

A certain asphalt-recycling factory is provided with a plant for blending, with heating, asphalt which had been used for the pavement of roads not less than 10 years ago, which was deteriorated with the elapse of time and which was peeled of from the roads and preliminarily heated, with approximately the same volume of fresh asphalt. The factory forwards the resulting blend to a road-paving site while the blend is still in its softened state. This factory is provided with a horizontal water-spraying scrubber at 2.5 m height from the ground surface for the purpose of the removal and deodorization of the black smoke giving out a bad smell and emitted from the plant during its operation and the smoke after washing or the exhaust gas is discharged into the atmosphere through a chimney having a height of 25 m. However, the scrubber never shows any cleaning effect and accordingly, black tar-like substances are settled down on and contaminate or pollute the areas of several tens meters square on the flatland and mountains and forests around the factory and the regional residents have always made a claim on the company.

Example 1

A cleaning agent, in the form of an aqueous solution, was prepared using 0.0006% of an amphoteric polymeric compound obtained by introducing 20% by mole of dimethylamino-methylacrylamide groups into 1 kg of a copolymer comprising 20% by mole of acrylic acid and 80% by mole of acrylamide and having an average molecular weight of $1.9 \times 10^7$; 0.001% of a poly(hexamethylene-biguanide) hydrochloride represented by the foregoing general formula (1) in which m=3, n=3 and p=12; 0.001% of glycine; and 0.001% of di-isopropanolamine. Using a double nozzle-type sprayer provided with a nozzle capable of forming mist having an average particle size of 15 μm as determined at the position situated at the distance, 30 cm, from the tip of the nozzle and having a spray angle of 15 degrees, the resulting cleaning agent was sprinkled into the exhaust gas emitted from the factory described in Reference Example 1, for about 2 minutes, at a rate of 120 mL/min as a flow parallel with the gas flow, while the nozzle was inserted into the chimney through the manhole having a diameter of about 30 cm at the position about 3 m apart from the bottom of the chimney of the factory specified in Reference Example 1 having a height of 25 m and the nozzle was inserted into the chimney in such a manner that it was approximately centered in the chimney. The black smoke was immediately disappeared during the spraying of the cleaning agent and it was assumed that the black smoke was downward descended or adhered to the inner wall of the chimney. Under the foregoing circumstances, the horizontal water-spraying scrubber was reconstructed by replacing the same with a vertical one so that the tar-containing substance settling down to the bottom thereof could easily be removed from the scrubber and could be introduced into an apparatus for softening the substance with heating. When the foregoing spray liquid was used in this reconstituted scrubber, the tar-containing substances settling down to the bottom of the scrubber could successfully and easily be withdrawn from the same.

[Cleaning of Exhaust Gases Containing Organic Volatile Substances and Mist of Paints and Varnishes Ejected from Painting Factories for Painting Automobiles and Household Appliances]

The exhaust gases emitted through small-sized painting booths in, for instance, small-scaled factories for repairing automobiles, factories for manufacturing automobiles and factories for painting household appliances are contaminated with volatile organic compounds (VOC) which are separated from paint mist which is not adhered to the face to be coated and whose concentration increases as the amount of the mist increases. The exhaust gas will highly be cleansed by sprinkling, into the same, the aqueous cleaning agent of the present invention having a low concentration.

Reference Example 2

In case of spray-coating of an object with an oil-based paint, only 30 to 80% of the solid content of the sprayed paint is adhered to the face of the object to be coated. Accordingly, the exhaust gas emitted from the coating booth is in general cleansed according to a widely used method which comprises the steps of washing the exhaust gas with an aqueous cleaning solution containing flocculating agents using a scrubber to thus separate adhesives of high molecular weight compounds and body pigments from the water-soluble organic solvents; removing them; and then adsorbing water-insoluble organic solvent on activated carbon particles.

However, it has been pointed out that this method suffers from a variety of drawbacks, for instance, specified below: the method is incomplete in the gas-liquid contact rate attained in the scrubber; the activated carbon undergoes the premature breakthrough due to the plugging up of fine pores thereof with the un-separated mist; the method involves a risk of causing a fire because of the insufficiency in the removal of the water-soluble organic solvents; the foregoing exhaust gas gives out an intensive bad smell; and it would be impossible or at least difficult to regenerate the used activated carbon in the breakthrough state, through a steam treatment.

Reference Example 3

In case of spray-painting with an oil-based paint, there have been adopted a variety of combustion methods for the purposes identical to those of Reference Example 2. However, the removal of the paint mist is often insufficient even when washing the exhaust gas emitted from the painting booth in a scrubber. In addition, it is difficult to achieve the complete combustion of the exhaust gas containing VOC and the gas flow obtained after the combustion gives out a bad smell. Accordingly, the exhaust gas should be deodorized, and this requires the use of activated carbon for the purpose of the deodorization through adsorption. Thus, there is such a contradiction that fresh activated carbon should be used for the regeneration of the used activated carbon in its breakthrough state by the steam-blowing technique and this combustion method further suffers from a problem in that the method may generate a large quantity of carbon dioxide which may serve as a cause of the variation of the earthly environment.

Reference Example 4

In case of the spray-coating with an oil-based paint, the method for spraying an aqueous cleaning agent could not remove the both paint mist and VOC at a high efficiency. There have likewise variously been tried the methods for spraying aqueous solutions of so-called plant's extracts or aqueous dispersions of perfumes, but the effects of these aqueous solutions and dispersions have not yet been elucidated or demonstrated.

Moreover, in case of the compositions comprising, as a main component, poly(meth)acrylamide as disclosed in parts of the disclosures of the aforementioned Patent Documents 1 and 2, the optimum degree of cleaning achieved at a relative humidity of not higher than 60% sometimes falls within the range of from 30 to 40% for the exhaust gas containing a part of water-insoluble solvents such as toluene and styrene, at ordinary temperature, but the exhaust gas emitted from the foregoing circumstances cannot be clarified at all when sprinkling a cleaning agent into the gas in the form of a gas flow having a high speed and a high humidity, and containing water-soluble solvents such as ethyl acetate, butyl acetate, and isopropyl alcohol.

Reference Example 5

As the spray paint used for repairing motorcars, there have recently worldwide been used one which comprises a straight acryl lacquer containing, as a vehicle, a copolymer of, for instance, a (meth)acrylic acid ester with styrene; or an NC-modified or CAB-modified acryl-acryl lacquer which simultaneously comprises the foregoing copolymer as a vehicle and nitrocellulose (NC) or cellulose acetate butyrate (CAB). These products per se and a thinner for the dilution of the lacquers in general contain a various kinds of low boiling point dilution solvents at high concentrations and accordingly, it has become an urgent problem awaiting solution to prevent the diffusion, into the exterior of the factories, of these dilution solvents in addition to the paint mist which is not adhered to the surface to be painted as well as the had smells of these materials. In this case, it is not possible to adopt the methods described in Reference Examples 2 to 3, from the technical standpoint.

For this reason, there has been desired for the development of a novel cleaning method which comprises the step of sprinkling an aqueous cleaning agent into the ducts for discharging exhaust gases.

Comparative Example 1

The straight acryl lacquer manufactured and sold by a paint-manufacturing company, which has been believed to be most widely spread in the world and the thinner specially designed for the straight acryl lacquer comprise the solvents as specified below, which was made open to the public by the foregoing company:

TABLE 1

| Solvents in Straight Acryl Lacquer (%) | | Composition of Thinner Specially Designed for the Lacquer (%) | |
|---|---|---|---|
| n-Butyl acetate | 40 to 50 | Ethyl benzene | 2.9 |
| Di-pentene | 1 to 5 | n-Butyl acetate | 50 to 55 |
| Ethyl benzene | 1.7 | Low boiling point aliphatic naphtha | 25 to 30 |
| Isobutyl alcohol | 1 to 5 | Xylene | 6.7 |
| n-Butyl alcohol | 5 to 10 | | |
| Xylene | 3.9 | | |
| Cellosolve acetate | 1 to 5 | | |
| Middle boiling point aliphatic naphtha | 1 to 5 | | |

The foregoing components (a) and (b) were uniformly blended at a standard mixing ratio of 62.5:37.5%, the resulting blend was maintained at a temperature of 20° C., for ensuring the constant discharged amount thereof, in a spray-painting booth [1.8 m (width)×2.7 m (length)×1.8 m (height) and 8.7 m³ (volume)] which was isolated from the external atmosphere, the trigger of the sprayer was fixed, and then painting was carried out using a double nozzle-type sprayer at a rate of 173 mL/min according to the real painting operation. A stainless steel duct having a circular cross section, a diameter of 800 mm and a length of 10 m was connected to the painting booth. Fresh air of the exterior of the booth was introduced, at an air flow velocity of 0.75 m/sec (0.377 m³/sec, 22.6 m³/min), into the booth through the duct using a fan for maintaining the amount of the paint mist containing the solvents to a level of not higher than the explosion limit thereof and for preventing the workers and operators within the booth from the poisoning from the solvents in accordance with the regulations stipulated in the Industrial Safety and Health Law. Thus, the exhaust gas was diluted with the air and then discharged from the booth. At this stage, the exhaust gas was sampled at the outlet of the duct and analyzed according to the gas chromatography technique (GC). As a result, it was found that the sum of the peak areas was 34,887 and the odor concentration as determined according to the three point-comparing odor-collecting bag technique (which was adopted by the Environment Agency) was 5,500. The temperature and the relative humidity during the tests were found to be 16 to 23° C. and 50 to 55%, respectively.

Comparative Example 2

The same procedures used in Comparative Example 1 were repeated to carry out the cleaning of the exhaust gas. More specifically, the cleaning liquid used herein was an aqueous liquid which comprised, per one liter of the liquid, 0.0005% of the amphoteric high molecular weight compound used in Example 1, as expressed in terms of the solid contents thereof; 0.01% of N-amino-1-propanol; and an aqueous dispersion of polyoxyethylene-lauryl ether having a cloud point of 55° C. and an HLB value of 12.0 and 0.005% of Zn—N-oxide 1-4 thiol as a preservative. The resulting cleaning liquid was sprinkled into the exhaust gas at the inlet of the duct, from which the gas was discharged, through three nozzles arranged at predetermined positions and directions on the duct as shown in FIG. 1, which could provide mist having a particle size ranging from 15 to 20 μm, at a flow rate of about 62 mL/min. On the other hand, the exhaust gas was sampled at the outlet of the duct during operation of the sprayer and the samples thus collected were analyzed by the GC according to the same procedures used in Comparative Example 1. As a result, the peak area was found to be 24,444 (reduction rate: 29.9%) in total, and the intensity or concentration of the odor was found to be 3600 (reduction rate: about 34.5%). The temperature and the relative humidity during the tests were found to be 19 to 24° C. and 48 to 52%, respectively.

Comparative Example 3

The same tests used in Comparative Example 2 were repeated except that the test was carried out on a rainy day in which the temperature and the relative humidity during the test fell within the range of from 27 to 32° C. and 88 to 93%, respectively. As a result, the peak area was found to be 32,044 (reduction rate: 8.1%) in total, and the intensity or concentration of the odor was found to be 3100 (reduction rate: about 13.91%). This indicates that the rate of cleaning is reduced under a high humidity condition.

Example 2

A cleaning liquid consisting of an aqueous solution was prepared, which comprised 0.0005% of a sol of the amphoteric high molecular weight compound used in Example 1, as expressed in terms of the amount of the anhydride thereof; 0.005% of poly(hexamethylene-biguanide) hydrochloride represented by the foregoing general formula (1) wherein m=3, n=3 and p=12, as expressed in terms of the pure compound; 0.02% of di-propylene glycol; 0.05% of ethyl glycol-adduct of 2-ethyl hexanol; 0.02% of methyl-propylene di-glycol; 0.05% of butyl di-propylene di-glycol; 0.005% of 1.5 mole ether-bonded product of glycerin and 2-ethylhexyl alcohol; 0.003% of a product obtained by adding 1.5 mole each of ethyl alcohol and oleyl alcohol to phosphorus pentoxide, then neutralizing the resulting product with 3.3 moles of di-isopropanolamine to thus make the product basic; and 0.005% of an aqueous dispersion of N-oxide 1-4 thiol as a preservative, as expressed in terms of the pure compound. The same procedures used in Comparative Example 2 were repeated except for using the resulting cleaning liquid. More specifically, the cleaning liquid was sprayed while collecting exhaust gas samples and they were analyzed according to the same method. As a result, the peak area was found to be 6,977 (reduction rate: 94%) in total, and the intensity or concentration of the odor was found to be 1030 (reduction rate: 81%), contrary to the results observed for Comparative Example 1. The temperature and the relative humidity during the tests were found to be 18 to 24° C. and 42 to 38%, respectively.

Example 3

The same procedures used in Example 2 were repeated except that a cleaning liquid was prepared by adding to the same cleaning liquid used in Example 2, 0.5% of common salt and 0.001%, as expressed in terms of the solid content, of a water-soluble product which was prepared by solution-copolymerizing, in ethanol, 28% by mole of a mixture containing acrylic acid and methacrylic acid and 72% by mole of methyl methacrylate in such a manner that the resulting product had a molecular weight of $2.1 \times 10^5$ and then neutralizing the product with aqueous ammonia. This cleaning liquid was sprinkled into the exhaust gas according to the same procedures used in Example 2. At this stage, the temperature and the relative humidity during the tests were found to be 18 to 21° C. and 86 to 89%, respectively. As a result of the analysis of the exhaust gas samples carried out according to the method identical to that used in Example 2, it was found that the peak area was equal to 6,977 (reduction rate: 80%) in total, and the intensity or concentration of the odor was equal to 1,450 (reduction rate: about 73.6%), contrary to the results observed for Comparative Example 1.

Example 4

The same procedures used in Example 2 were repeated except that the temperature and the relative humidity during the tests were found to be 20 to 22° C. and 88 to 92%, respectively, that separate 2 spray nozzles each were arranged, within the duct, at a position located at 2 m behind the second and third cleaning liquid-spray nozzles and at a position situating about 50 cm ahead of the demister arranged at the position located behind the exhaust port so that a 10% aqueous solution of sodium sulfate was sprayed immediately after the spraying of the cleaning liquid to thus convert the sol-like cleaning liquid into a gel or liquid drops and to thereby permit the immediate discharge thereof to the exterior of the duct. As a result of the analysis of the exhaust gas samples, it was found that the peak area was equal to 2,160 (reduction rate: about 93.8%) in total, and the intensity or concentration of the odor was equal to 275 (reduction rate: about 95%), contrary to the results observed for Comparative Example 1.

Example 5

In this Example, the aqueous solution prepared in Example 2, as a cleaning liquid, was sprayed in a duct containing an exhaust gas under the conditions where the temperature and the relative humidity during the tests were 18 to 23° C. and 88 to 94%, respectively, while a 0.001% by mass aqueous solution of the ammonium salt of water-soluble acrylic copolymer used in Example 3, as a gelling agent, was perpendicularly sprayed, in the form of mist having a particle size of 15 μm, on the spray mist of the cleaning liquid through a nozzle attached to the side wall of the duct and arranged at a position located at 2 m behind the second and third cleaning liquid-spray nozzles, at a rate of 20 mL/min. The liquid converted into droplets and settled down within the duct was externally discharged from the duct through a pit arranged within the duct. The exhaust gas was sampled and analyzed in the same manner used above and as a results, it was found that the peak area was equal to 3,488 (reduction rate: about 90.0%) in total, and the intensity or concentration of the odor was equal to 440 (reduction rate: about 92%), contrary to the results observed for Comparative Example 1.

Example 6

A sheet of filter paper having a width of 20 cm and a length of 2 m was adhered, using a double-coated adhesive film, to the internal face of a polyethylene bag, along the longitudinal direction thereof, which was converted into a cylindrical shaped bag having a length of 3 m and a diameter of 30 cm, when closing the both ends thereof and filling the same with air, 10 U-shaped magnets were then adhered to the polyethylene bag at equal intervals using the same double-coated adhesive film. A rubber tube having an inner diameter of 15 mm for the introduction of contaminated air (a gas-introduction port) and the nozzles of a double nozzle-type sprayer capable of generating mist having an average particle size of 16 μm for spraying the cleaning liquid were inserted into the polyethylene bag through the left-hand side end thereof and they were fixed by fastening tightly with a string. On the other hand, the same rubber tube for the exhaustion was inserted into and fixed to the bag at the center of the right-hand side end. The temperature and humidity conditions within the bag during the tests were set at levels ranging from 18 to 23° C. and 88 to 90% respectively. In this Example, the contaminated air used in Example 3 was introduced into the bag through the gas-introduction port and discharged through the exhaust port thereof at a flow rate of 25 L/min while the cleaning liquid used herein was prepared by adding, to the cleaning liquid of Example 3, 0.0003% by mass of a magnetic fluid which was prepared by blending the formulation used in Example 1, 30 g of magnetite particles having an average particle size of 300 nm, 5 g of a sodium alkylbenzene-sulfonate and 65 g of water and then stirring the resulting mixture to give a dispersion. This cleaning liquid was sprinkled into the bag at a rate of 10 mL/min for 3 minutes. The exhaust gas sample collected at the end of the bag through a Y-shaped valve fitted to the rubber tube arranged at the outlet port was inspected for the intensity or concentration of odors thereof and it was found to be 900 (reduction rate: 81%). Further, a significant amount of contaminants was found to be adhered to the both poles of the U-shaped magnets arranged within the bag and there was observed the presence of sprayed mist which was dropped and arranged along the lines of magnetic force.

[Removal of Odors Emitted from Putrid Smells of Proteins and Removal of Dust Comprising Harmful Microorganisms Through Settling]

Reference Example 6

It would be assumed that the exhaust gas emitted from the factory in which box lunches (hereunder referred to simply "raw material") whose shelf life (sell-by date) had been expired were collected and fermented using microorganisms under anaerobic growth conditions to thus prepare compost consisted of a large number of bad smell-emitting substances, the composition of which could not precisely be grasped, in low threshold levels, while taking into consideration the chemical analysis carried out according to the GC technique. However, the results obtained according to the GC analysis indicated that the exhaust gas was comprised of low and middle fatty acids, low and middle aliphatic aldehydes and mercaptans and that the composition of the exhaust gas was considerably changed depending on the kinds of the raw materials used and the term elapsed after the introduction of these raw materials into the compost-making process. In addition, within the workshop, microorganisms and spores thereof, suspensible dust of the products were scattered in the workshop along with the bad smells emitted therefrom during the step for turning the pile of the compost upside down and mixing by stirring. Accordingly, the possibility of the workers may inhale these fungi and may thus be attacked with certain infectious diseases at a high probability. For this reason, an aqueous solution of wood-derived vinegar apprehensive of having toxicity was sprayed as a countermeasure for the solution of these problems. However, the inhalation of the wood-derived vinegar has been proved to be undoubtedly detrimental to the workers and therefore, there has intensively been desired for taking a real measure to overcome this problem from the viewpoints of the workers safety in the operations and the prevention of any diffusion of contaminated air even to the neighboring residence sections.

Comparative Example 4

An aqueous solution was prepared, which comprised 0.0006% of a sol of the amphoteric high molecular weight compound described in Example 1, as expressed in terms of the amount of the solid content thereof 0.005% of a 0.005% aqueous solution of Zn—N-oxide 1-4 thiol (a preservative), as expressed in terms of the amount of the solid content thereof and 0.1% each of potassium bicarbonate and sodium carbonate. The resulting aqueous solution was sprinkled, in place of the wood-derived vinegar, onto the pile of the compost, through a fluid sprayer attached to the prop of an apparatus for turning the compost upside down and mixing by stirring, at a height of 3 m, while facing the sprayer downward, wherein the sprayer could form mist particles each having a particle size of 20 μm. As a result, the transparency of the surrounding space, after the spray of the aqueous solution, increased and therefore, it was recognized that the spray of the aqueous solution certainly resulted in the achievement of an effect of settling the dust suspended in the space. In this respect, the quantity of odors present therein was considerably reduced because any wood-derived vinegar was not used, but the deodorization was found to be still incomplete from the viewpoint of the olfactory sense. More specifically, the exhaust gas analysis carried out immediately after the spray of the aqueous solution using a gas-detection tube at a height of 1.5 m from the surface of the raw material indicated that the concentration of lower fatty acids was found to be 0.0015% by volume (15 ppm) as expressed in terms of the concentration of acetic acid, and that of lower aldehydes was found to be 0.0015% by volume (15 ppm) as expressed in terms of the amount of acetaldehyde.

Example 7

An aqueous solution was prepared, which comprised 0.0005% of a sol of the amphoteric high molecular weight compound of Example 1 as expressed in terms of the amount of the solid content thereof; 0.06% of di-propylene glycol; 0.006% of the poly(hexamethylene-biguanide) hydrochloride represented by the foregoing formula (1) in which m=3, n=3 and p=12, as expressed in terms of the polymer moiety thereof; and 0.5% of di-isopropanolamine. The resulting aqueous solution was sprinkled on the compost according to the same procedures used in Comparative Example 6. As a result, it was found that the aqueous solution showed more excellent effect of settling dust, the concentration of lower fatty acids, as expressed in terms of acetic acid, was found to be 0.0005% and that of lower aldehydes, as expressed in terms of acetaldehyde, was found to be 0.0003%. However, intensive bad smells were still detected in the exhaust gas and the atmosphere within the factory. Then, an aluminum flexible pipe having a diameter of 30 cm was fitted to the wall of the closed factory at a height of 5 m from the floor of the factory and connected to a scrubber such as that disclosed in the foregoing Patent Document 5 or 6. Subsequently, the exhaust gas consisting of a contaminated air flow drawn from the factory using a ventilation fan was passed through the scrubber in which the foregoing cleaning liquid was charged and circulated. As a result, the concentrations of the both lower fatty acids and lower aldehydes were found to be zero, when they were determined according to the analysis using a gas-detection tube and the concentration or intensity of the odors as determined by the simple three point comparative odor-collecting bag technique was found to be 30. The scrubber used herein was a portable one for laboratory use, which had an inner volume of 200 L, which was provided with a laminated layer of fillers made of paper to which water-resistant characteristics had been imparted and which had a ventilation capacity of about 400 L/min. It was thus suggested, on the basis of the satisfactory results obtained in the foregoing small-scale trial carried out while making use of the spray technique and the scrubber-cleaning technique, that the client should adopt a method in which the combination of these two techniques are scaled up.

Reference Example 7

Natural rubber used as a principal raw material for forming the sheaths of electric wires, tires and other various applications is quite susceptible to putrefaction since it comprises acetic acid and about 3% of proteins incorporated into the same as a coagulant for the latex and accordingly, gave out very intensive bad smells containing various components like those listed above in connection with Reference Example 6. Moreover, in this mastication step, a mixed preparation, which comprises contaminated putrefactive bacteria or fungi and the spores thereof, and auxiliary additives, in particular, carbon black, pentaerythritol esters, waxes, and calcium carbonate, is added to the natural rubber in the step carried out in a closed kneader at a temperature of not less than 120° C., or in the mastication step carried out at a temperature of not less than 65° C. in an open roll machine together with other additives such as fine powdery 2-benzamide-thiophenol. At this stage, there would be generated, in addition to the foregoing bad smells, dust due to the use of such fine powdery flowability improvers and the foregoing heating and/or blending steps and tar-like contaminants in the form of an aerosol in a high concentration and accordingly, the exhaust gas emitted from the factory comprises the combination of the foregoing various components and it is thus contaminated in a high degree. To make clean the atmosphere within a certain tire-manufacturing factory and/or the exhaust gas emitted from the tire-manufacturing factory, an aqueous liquid was sprinkled into the duct, which comprised a formulation of so-called phytoncide and polyphenol type plant's extracts, but any cleaning effect could not be detected other than the fragrance-imparting effect.

Comparative Example 5

On a duct for the both exhaustion and cleaning of the exhaust gas, which has a diameter of about 80 cm and a rate of exhaustion of about 800 m³/min, and which is arranged in a certain rubber-mastication factory, there were installed three double nozzle-type sprayers at about 5 m intervals, in which each sprayer can generate mist having an average particle size of 16 μm, has a spray angle of 30 degrees, the direction of the spray is parallel to the gas stream and each of the capacity of spraying a liquid thereof is 40 mL/min. Then there was sprinkled, into the duct, an aqueous dispersion which comprised 0.0006% of the amphoteric high molecular weight compound used in Example 1, as expressed in terms of the solid content; 0.0001% of di-isopropanolamine; 0.002% of methyl-propylene diglycol; and 0.005% of Zn-pyrithione (an anti-fungal agent) and then the exhaust gases collected at the inlet and the outlet of the duct were inspected for any change in the intensity of the smell. As a result, the rate of reduction in the concentration of odors as determined by the three point-comparative odor-collecting bag technique was found to be 38% and this indicated that a slight reduction of the odors was detected in the exhaust gas collected at the outlet of the duct, but strong bad smells were still detected. In addition, in the liquid reservoir for accumulating and draining the waste liquor in the form of liquid drops, which is disposed within the duct, it was also observed that a considerable amount of sticky, dark brown-colored tar-like liquid which gave out intensive bad smells, stayed and remained in the liquid reservoir.

Example 8

In this Example, the same apparatus installed in the same factory used in Comparative Example 5 and it was operated under the same conditions used therein. There was then sprinkled, into the duct, an aqueous dispersion prepared by further adding, to the aqueous spraying dispersion used in Comparative Example 7, 0.01 g of di-propylene glycol and 0.04% of poly(hexamethylene-biguanide) hydrochloride represented by the foregoing general formula (1) in which m=3, n=3, and p=12. As a result, it was found that the odor detected at the outlet of the exhaust duct was considerably reduced in the light of the olfactory sense and, in fact, the rate of reduction in the concentration of the odor was found to be 95% as determined at the outlet of the duct.

Comparative Example 6

Possible air-contaminating substances generated from the surface of the interior of closed or semi-closed rooms such as newly-built houses, guest rooms of hotels, business offices, sickrooms, care rooms, air-conditioners, airplanes, warships and other vessels, and trains may include, for instance, oil-based paints and varnishes, perfumes, formaldehyde, detrimental gases and VOC or the like such as insecticides, smells of tobacco, evil body smells, detrimental bacteria and fungi, mold, viruses, and smells associated with cares, but there has not yet been developed any technique for completely and comprehensively deodorizing, detoxifying, sterilizing, and disinfecting those listed above. For instance, Patent Document a: Japanese Patent No. 2,134,708 discloses a method, which comprises the steps of preparing an aqueous solution comprising 0.0005% of an amphoteric high molecular weight compound having a structure to which 20% by mole each of carboxyl groups and dimethyl-aminomethyl(meth)acrylamide groups are bonded and which has a molecular weight of $1.0 \times 10^7$; 0.001% of 2-aminomethyl-1-propanol; and 0.03% of an aqueous dispersion of Zn-pyrithione as expressed in terms of the compound per se and then spraying the resulting aqueous solution onto the surface on which the foregoing contaminants are adsorbed. However, the results obtained indicated that the aqueous solution never adhered to the hydrophobic surface of, for instance, wall paper made of vinyl chloride clothes, and interior materials and carpets made of polyester fibers, the solution was dropped out of the same after drying them and it did not show any contaminant-removing effect. On the other hand, the aqueous solution could completely remove the bad smells and part of body smells penetrated into hydrophilic bedclothes such as blankets made of cotton or wool, but it never showed any effect of deodorizing, for instance, the smells of cigar, perfumes, VOCs, moldy smells and those of insecticides.

Example 9

In this Example, an aqueous solution was prepared by adding, to the cleaning liquid prepared in Example 1, 0.06% of di-propylene glycol; 0.03% of a 0.006% aqueous dispersion of Zn-pyrithione as expressed in terms of the compound per se, and 0.001%, as expressed in terms of the solid content, of a polymeric product having a weight average molecular weight of $2.0 \times 10^5$, and obtained by solution-polymerizing 27% by mole of (meth)acrylic acid and 73% by mole of a mixture containing methyl acrylate and ethyl acrylate, in ethyl alcohol, subsequently removing the ethyl alcohol through distillation, and then neutralizing the product with ammonia. The resulting aqueous solution was sprinkled into a guest room of a hotel in which contaminants had been adsorbed on the internal surface thereof and which had a total surface area of about 33 m². More specifically, the aqueous solution was sprinkled into the guest room for 2 minutes/room, using a portable sprayer capable of generating mist having a particle size of 12 μm at a rate of 12.5 mL (sprayed liquid)/min and thereafter the room was ventilated for about 5 hours at ordinary temperature to thus completely dry the room. It was confirmed, on the basis of the results of the real works executed by 5 companies for cleaning houses and for cleaning air-conditioners, that the dried gel of the sprayed mist was not dropped off, that the aqueous solution could completely remove body smells including the smells of the armpit which could not removed by the conventional method such as that disclosed in Comparative Example 8, the smells of perfumes, the smells of cigar, the smells of incense sticks, and the moldy smells and that the deodorization and anti-fungal effects could further be maintained for a term ranging from 6 months to not less than one year although the effects would be dependent upon the use conditions of each room.

Example 10

Regarding private rooms of a newly-built multistoried apartment house in a certain country, which is full of strong irritative smells to such an extent that anybody cannot live in, there were sampled, in odor-collecting bags, the atmosphere of the foregoing private room which is full of the smells of chemicals originated from the coated materials and construction materials used within the room, prior to any treatment. Then the aqueous solution prepared in Example 7 was sprayed on the whole internal surface of the room using a double nozzle-type sprayer capable of generating mist having a particle size of 15 μm at the position 30 cm apart from the nozzle tip. The aqueous solution was sprayed onto the inner surface from the position 40 to 100 cm apart from the face to be treated at a rate of about 2 mL/m$^2$, followed by air drying over about 24 hours, ventilating the room for 2 hours using a ventilation fan, and then allowing the room to stand for 48 hours. After the completion of these treatments, the air within the room was collected and analyzed by the gas chromatography technique. Thus, the results as shown in the following Table 2 were obtained.

TABLE 2

| VOC Gas Sample Tested (%) | Benzene | Toluene | Formaldehyde | Note) Olfactory Intensity |
|---|---|---|---|---|
| Conc. prior to the treatment | 0.00018 | 0.00012 | 0.000310 | Quite strong |
| Conc. after to the treatment | — | — | — | Not detected |

Reference Example 8

Visible contaminants are attached to and/or adsorbed on the interior surface of, for instance, business offices, second-hand houses, inns and hotels, which have been used over not less than 20 years after the construction thereof, in particular, carpets, equipments for cooking, and air-conditioners and more specifically, the visible contaminants include, for instance, (a) depositions of soot originated from the exhaust gas emitted from motorcars, fine dust and mud; (b) spots or dirt of foods and drinks including coffee, adhered to, for instance, carpets; (c) fungi and mites which live in or grow or proliferate on, for instance, carpets and portions situating ill-ventilated areas within a room; (d) soot originated from exhaust gases, hardened oil films and mist emitted during cooking, which are adhered to the filters for exhaustion in the kitchen, the periphery thereof and the whole internal surface of the cooking room; (e) the contaminants listed in the foregoing item (a) and (c) deposited on the aluminum heat-exchanger and ventilation fan in an air-conditioner; (f) excrements of insects and birds. In most of the foregoing cases, the cleaning and wiping of the foregoing contaminated articles as the objects to be cleansed were carried out by applying, onto the surface of the object to be washed, an aqueous solution of a strong alkaline substance having a pH value not less than 12, to which a variety of surfactants are added, through spraying; and then washing by applying a jet of water to the surface under a high hydraulic pressure on the order of not less than 10 kg/cm$^2$. Accordingly, the object to be washed may often be damaged. Alternatively, the contaminants are sometimes scratched off using a scraper and in this case, the surface of the object may likewise be damaged. In any case, the surface of the object may undergo change of color and intensive bad smells still remain even after the washing, in most of cases. In particular, a variety of presently existing cleaning agents which comprise strongly alkaline substances and surfactants have been used for cleansing the oxidized oil films which give out intensive bad smells and formed within the air-conditioners used in, for instance, Chinese restaurants, Tempura shops or restaurants and grilled meat restaurants, but these existing cleaning agents do not have any substantial cleaning effect and accordingly, it has presently been considered to be impossible to completely remove the foregoing contaminants consisting of oxidized oil films. For this reason, the service life of these articles is quite short on the order of 1 to 2 years this in turn leads to the waste of electric power and an increase in the risk of causing a fire.

Comparative Example 7

The washing companies specified in Example 7 used a cleaning composition disclosed in Patent Document 3, which comprised 50 g of a copolymer of acrylamide (90%) and acrylic acid (10%) having a molecular weight of $1.5 \times 10^7$; 579 g of sodium metasilicate 250 g of anhydrous sodium sulfate; 100 g of sodium percarbonate monohydrate; 10 g of fine powdery zeolite; 1 g of an equivalent mixture containing perfluoroalkyl-containing activator and ethylene oxide/propylene oxide copolymer type activator; and 10 g of sodium oxalate, for the cleaning and wiping and washing of contaminated objects. As a result, it was found that the cleaning agent was proved to be effective for the removal of fine duct such as soot and dirt among the contaminants adhered to various kinds of objects, while the cleaning effect thereof was insufficient for the removal of the foregoing oxidized oil films and spots or stains formed on carpets and that the cleaning agent was likewise proved to be insufficient in the sustained bacteriostatic effect on fungi.

Example 11

A cleaning liquid was prepared by preparing an aqueous solution containing 73 g of a water-soluble amine soap obtained by reacting one mole of oleic acid, 0.2 mole of tri-isopropanolamine and one mole of di-isopropanolamine; 50 g of di-propylene glycol; 10 g of poly(hexamethylene-biguanide) hydrochloride represented by the foregoing general formula (1) in which m=3, n=3 and p=12; 0.04 g of a sol containing an amphoteric acrylamide polymer having a molecular weight of $2.0 \times 10^7$ and comprising 25% by mole of (weth)acrylic acid moieties and 25% by mole of dimethylamino-methylacrylamide moieties; 8 g of Zn-pyrithione (an anti-fungal agent) and the balance of water (an amount required for making the total volume of the resulting solution 1 kg); then diluting the resulting aqueous solution 30 times (by volume) with warm water heated to about 45° C. The cleaning liquid thus prepared was first sprayed, through a plastic manually operable spray pump, on strongly contaminated portions among the spots and/or stains of foods and drinks which had been adhered to the carpet used under the dining tables in the buffet of a certain cruising passenger boat, which gave out bad smells and which could not be removed by the conventional cleaning agents and/or cleaning methods, to thus moisten or dampen the portions with the solution over a time period ranging from 30 minutes to one hour; putting the carpet in a cleaning machine manufactured and sold by SANKYO Aqua-system Company provided with a negative pressure or vacuum type nozzles, which permitted the cleaning of objects without moistening the floor with the cleaning liquid to thus make clean the carpet. As a result, the dirt with fine dust such as spots and stains could completely be removed and the cleaning liquid could impart sustained deodorization and bacteriostatic effects to the carpet. These effects had already been confirmed using preliminary tests. Thus, the atmosphere in the buffet could be improved and the atmosphere thereof thus gave a refreshed feeling.

Example 12

The whole surface of the wall paper made of PVC and the doors made of decorated plywood of a kitchen-dining-room in a certain wooden house which had been completed and occupied for not less than 30 years were contaminated with hardened and blackened oil films provided with adsorbed soot, for which any conventional cleaning agents never showed any effect of removing the same. When a dustcloth was moistened with the same aqueous solution prepared in Example 11 and the foregoing surface was cleansed and wiped with the dustcloth impregnated with the aqueous solution, the oil films were completely been removed together with the soot adsorbed thereon, soil and proliferated mold or colony of mold or fungi, the beautiful appearance almost identical to that observed when the house had been completed could be recovered, all of the bad smells adsorbed on the whole surface of the room completely disappeared and any odor of the cleaning agent could not be detected in view of the olfactory sense.

Example 13

In a certain Chinese restaurant, the outer surface of a wall type air-conditioner disposed in the cook room and used over about 2 years, which should be replaced with new one was contaminated with mist originated from the cooking and the aluminum heat-exchanger and the plastic fan included in the air-conditioner were likewise contaminated with black-colored oil films adhered to the surface thereof. As a result, the air-cooling and air-heating functions thereof were significantly reduced and the internal spaces of the cookroom and the eating room were full of strongly bad smells emitted therefrom. To make them clean, the electric circuits of the air-conditioner including the distributing wires were covered with a waterproof plastic film to thus protect the electric circuits and the distributing wires from coming into contact with any cleaning liquid and preventing any leakage of the cleaning liquid in the conditioner; and the air-absorbing plane and air-discharge plane as well as the whole fan of the heat-exchanger were likewise covered with a plastic film to thus make the cleaning liquid drop down so that the dropped cleaning liquid could be received and accommodated in an accumulation container. At this stage, the cleaning agent of Example 11 diluted 30 times with water was sprinkled into the air-conditioner for about 2 minutes through a double nozzle-type sprayer capable of forming mist having a particle size of 20 µm to thus entirely moisten the heat-exchanger and the fan, followed by allowing them to stand over about 30 minutes and then applying, to the same parts, a jet of the same diluted aqueous cleaning solution at a hydraulic pressure of 10 kg/cm$^2$ for 5 minutes using a jet-type washing machine. Dark black-colored waste liquor was dropped into the accumulation container, while the surface of the heat-exchanger initially having dark black color was immediately cleansed and the washed heat-exchanger was thus regenerated into one having a silvery color like the new one. The heat-exchanger was further washed over 203 minutes, followed by drying the same with ventilation, spraying the cleaning agent of Example 1 onto the heat-exchanger for 3 minutes using a sprayer capable of forming mist having a particle size of 15 µm, drying the same and then it was confirmed that the cold air flow free of any bad smell was discharged from the same.

Comparative Example 8

Two sheets of lace curtain made of polyester fabric which had continuously been used over about 10 years after purchasing the same and which had frequently been brought into contact with the open air were contaminated with, for instance, sand dust, the smoke discharged from motorcars, secretions derived from various insects and the nicotine of tobacco. Then, both of these sheets of lace curtain were washed in a household washing machine containing 40 L of water and 30 g of a powdery detergent for 10 minutes, followed by the rinse thereof with water and then spreading and drying the same without squeezing the water out of the lace curtain. As a result, the whiteness degree thereof could not be recovered sufficiently, but they were dried without any post-treatment.

Example 14

The two sheets of lace curtain washed in Comparative Example 9 and additional two sheets of lace curtain identical to those used in Comparative Example 9 prior to washing (4 sheets of lace Curtain in all) were immersed in 10 L of the cleaning agent prepared in Example 8 which was diluted 30 times with water for 10 minutes, followed by washing them with 40 L of water for 10 minutes in the same washing machine used in Comparative Example 9 and drying them in the same manner used therein. As a result, it was confirmed that the whiteness degree of the resulting lace curtain was considerably improved.

Example 15

The applicant asked a certain laundry to spray shirts, in particular, the neck and cuffs as well as the stained portions thereof with the cleaning agent prepared in Example 11 which was diluted 30 times with water, through a plastic spray pump, when he was entrusted with the cleaning of shirts, and subsequently to wash them according to the usual washing or cleaning method after the elapse of time ranging from one hour to overnight. As a result, the fats excreted by the human body adhered to the foregoing portions of each shirt were completely eliminated, this accordingly eliminated the requirement for the strong rubbing of the stained portions with a bamboo whisk which might greatly damage the fibrous material, the resulting shirts had excellent hand and feel without using any softening agent, the evil smells of the armpit was never transferred from shirt to shirt, the next washing thereof would become easy, any bad smell was not generated during the ironing and press-finishing of the same. Thus, it would be concluded that the cleaning agent of the present invention permitted the solution of the problems common to this field.

Reference Example 9

The contaminated clothes, in particular, European clothes made of wool and Japanese clothes (Kimonos) made of silk as well as ties cannot be washed with an alkali aqueous solution since they undergo shrinkage and the deterioration of fabrics or fibers and therefore, they have in general been washed according to the dry cleaning technique which makes use of volatile organic solvents. However, chlorinated ethylene showing quite excellent effect of removing oil-containing contaminants is strongly detrimental or toxic and therefore, it is strictly limited in its practical use to quite narrow applications because of the recent strengthened regulations relating to the penetration and permeation thereof into underground water and the prevention of the environmental pollution. For this reason, there have presently been used, for instance, paraffinic hydrocarbons whose solubility in oils and fats is low as compared with that of an aromatic hydrocarbon or a naphthenic hydrocarbon, and there has been used, in Japan, JIS industrial gasoline No. 5 (which corresponds to Stoddard solvent in the United States and White spirit in Great Britain). More specifically, the soap for the dry cleaning presently used is a solution prepared by incorporating, into the foregoing paraffinic hydrocarbon, an aqueous solution of an oil-soluble surfactant, water and a co-solvent for the water such as an alcohol or cellosolve in an amount of not less than the solubility thereof. However, the resulting cleaning agent for the dry cleaning has an extremely low rate of removing contaminants. Accordingly, if the clothes treated according to the presently used dry cleaning technique are subjected to the steam-ironing process, the clothes often give out bad smells, except for those subjected to high quality finishing treatment. For this reason, if the clothes thus treated are washed with water without any pre-treatment, the water used in the washing step soils and the color thereof is changed into block.

Examples 16 to 18

A mixed thermally-bonded lace comprising 60% of vinylon fibers and 40% of polyester fibers having a perforated pattern, JP4532B-056 OB-SK-P (available from Kuraray Co. Ltd.) was folded in two, a spun-bonded nonwoven fabric of a 1:1 mixture of rayon and polyester was sandwiched between the folded lace and then they were joined by stitching to thus give a cleaning and wiping cloth. The resulting cloth was immersed in the cleaning agent of Example 11 diluted 30 times or 60 times with water followed by squeezing the solution out of the cloth, rubbing and/or wiping the face and back of the clothes specified below whose wearing frequency was high in the winter season to sufficiently remove contaminants adhered thereto, and then finishing the clothes by subjecting them to the steam-ironing (method A) or air-drying the clothes while hanging out them from a pole, after they were immersed in the aqueous solution, with gently crumbling, to make clean them (method B).

The advantages of these treatments from the viewpoint of the environmental protection are that they do not use any solvent for the dry cleaning, whose recovery through distillation is difficult, and that the processing liquids used in these Examples each have an extremely low concentration and the oils and fats moieties can be recovered, if necessary, through the addition of an acid. Further advantages of these treatments are, for instance, as follows: The finishing treatments used in these Examples permit the complete removal of stains and soot attached to and adsorbed on clothes; any bad smell generated from the clothes due to the dry cleaning process cannot be detected at all during the ironing treatments; the clothes finished by these treatments are flexible; they exhibit good hand and feel with bulky feeling; they do not give out any smell of chemicals; they are never accompanied by any proliferation of fungi; they are hardly contaminated with dirt and bad smells through adhesion or absorption; they can repeatedly be subjected to the same treatments; and the production efficiency may be improved by the development of a specially designed machine.

Reference Example 10

It would be a very important subject to treat rotten liquid and slurry which give out bad smells and/or generate detrimental gases and in which harmful microorganisms are growing. For instance, (a) the waste liquor discharged after the urinalysis of a large number of persons in the medical examination also comprises urines excreted by those suffering from visceral organs and genital organs and therefore, emanates or generates unpleasant bad smells, droplets containing detrimental and pathogenic bacteria and viruses may diffuse throughout the room and accordingly, there would be such a risk that the staffs concerned may be infected with a disease caused by such bacteria or viruses through the inhalation of such droplets thereof scattered when disposing these urines to toilet, drainage or a bucket. (b) The waste liquor of refreshing beverages containing sugars in a high concentration would be quite susceptible to the putrefaction within a very short period of time give out extremely and highly intensive mixed bad smells containing, for instance, acetaldehyde, lower fatty acids, lower aliphatic aldehydes, whose threshold values are low, these smells may attract, for instance, various kinds of flies and bees and wasps which may sting and/or bite men and beasts to thus adversely affect the peripheral region, because of the foregoing unpleasant smells and risk.

Examples 19 and 20

Each of the foregoing subjects (a) to (c) listed above in connection with Reference Example 10 could be solved by the use of the cleaning agent according to the present invention due to the bactericidal, detoxicant and antiseptic effects of the cleaning agent.

TABLE 3

| Ex. No. | Kind of Clothe Tested | Dilution Factor (fold) | Amt. of Processing Liquid Adhered (%), (prior to drying) | Method of washing, finishing |
|---|---|---|---|---|
| 16 | Coat and trousers of suit made of wool (with lining) | 30 | 25 | Method A |
| 17 | Cotton corduroy coat (with lining) | 30 | 20 | Method A |
| 18 | White woolen sweater | 60 | 350 | Method B |

TABLE 4

| Ex. No. | Origin of Contaminated Air | Method of adding cleaning agent | Resulting effect | Formulation of processing liquid |
|---|---|---|---|---|
| 19 | Reservoir for examined urines | Injected into the container in advance | Deodorization, antibacterial effect, and effect of preventing the scattering of droplets | Cleaning agent of Example 1 concentrated to a conc. 5 times higher than that of the original |
| 20 | Container for receiving waste refreshing beverages containing sweetener | Injected into the container in advance | Effect of preventing the attraction of any insect, in addition to those listed above | The processing liquid used in Example 19 in which 5 g/L of sodium sulfite was dissolved |

Reference Example 11

The air-filter for air-conditioners can remove coarse dust, but it was found to be ineffective for the removal of detrimental aerosol-like contaminants such as dust, the smoke of tobacco, bacteria and viruses. In addition, the usual gauze mask was likewise found to be ineffective for the removal of dust. Moreover, a high performance dust-proof filter for dust-free rooms (usually abbreviated as "HEPA") can remove very fine dust, but it has a high resistance to ventilation and accordingly it is considerably limited in its applications.

Comparative Examples 9 and 10 and Example 21

There were provided gauze masks for adults each having a weight of 5.1 g, each of which was prepared by stitching 6 layers of cotton gauze having a size of 9 cm (height)×13 cm (width) and then attaching rubber strings to the both selvages thereof, and dust-proof masks of cotton gauze having a weight of 2.6 g, which comprised of a sheet of gauze cloth folded in three layers having a size of 7 cm (height)×9.5 cm (width) and two gauze pads. Five sets each of these masks were immersed in the cleaning liquid having the formulations as will be specified below, subsequently the masks were centrifuged to remove the cleaning liquid from the same to such an extent that the liquid-inclusion rate (pickup) thereof of 250±10% on the basis of the weight of gauze, followed by drying them in a thermostatic air-circulated dryer till the weight of each sample became constant, and then allowing them to stand overnight under ordinary temperature and humidity conditions. Then masks (A) free of any treatment, the masks (B) subjected to the treatment of Comparative Example 10 and those (C) subjected to the treatment of Example 19 were handed to two workers engaged in the cleaning of air-conditioners. Each worker was requested to conduct the cleaning of air-conditioners while wearing one kind of the mask (A) to (C) per day, to judge the ability of each mask to trap dust, which was evaluated on the basis of the degree of contamination of the mask and the olfactory degree of the bad smells and to report these results. Thus the results as detailed below were obtained:
[Formulation of Cleaning Liquid Used in Each Test]

Comparative Example 9

Free of any Treatment;

Comparative Example 10

The cleaning liquid used in Example 1 except that it did not contain any poly(methylene-biguanide) hydrochloride and that the cleaning liquid was concentrated to 5 times the original one;

Example 21

An aqueous solution containing the components used in Example 1 in which each component was used in an amount 5 times that used in Example 1.
[Results of the Olfactory Degree of Bad Smells Detected and Contaminated Degree of Each Mask and Gauze Pad]

Comparative Example 9

The intensity of the bad smells detected was almost identical to that detected when the worker did not wear the mask. The mask was contaminated by the adhesion of a small amount of dust. In addition, the dust adhered to the surface of the mask taken off after the working could be detected when touching the same with the hand.

Comparative Example 10

The worker judged that the intensity of the bad smells was considerably reduced. It was further found that the regions on the mask near the nares of the wearer were significantly contaminated with dust.

Example 21

When the worker started to wear the mask and the region thereof near the flares was expanded by the action of the breath to thus form water-absorptive gel, the wearer felt almost no bad smell. Dust was more conspicuously adhered to the region of the mask near the nares during wearing the mask. Thus the wearer recognized that there was not any risk of absorbing detrimental gases and dust during wearing the mask and he could conduct the cleaning operation with a sense of security.

As has been described above, it was thus confirmed that the mask treated according to the present invention could immediately undergo swelling by the action of the moisture present in the highly humidified breath discharged from the nares of the wearer to thus form a gelled layer and that the treatment of the present invention could protect the wearer from the absorption of any detrimental fine dust and the bad smells and harmful gases present in the workshop or working environment to thus prevent the wearer from injuring the health and prevent the wearer from having any unpleasant feeling.

Comparative Example 11

It is rarely the case that only one kind of good is continuously produced over a long period of time in the manufacturing and packaging factories in the fields of, for instance, refreshing beverages, green tea, lactic acid-fermented beverages, and liquid seasonings. More specifically, it is common that one kind of good is manufactured and packed, thereafter the pipes for packaging or the like are subjected to stationary washing (CIP washing or cleaning) and another kind of good is subsequently manufactured and packed. In such a case, if the previous good remains in, for instance, the packaging tank and distributed piping, even in a very small amount, the taste and texture as well as the flavor of the previously manufactured good may be transferred to the subsequently manufactured product and the commercial value of the latter good is considerably reduced. In a certain factory, the cleaning of the foregoing parts is carried out according to the following steps:

The order of these steps is as follows: (1) a step of washing with hot water (at 85° C. for 30 minutes)→(2) a step of washing with hot water (at 85° C. for 30 minutes)→(3) a step of washing with a 2% aqueous solution of caustic soda→(4) a step of washing with a 2% aqueous solution of nitric acid→(5) a step of washing with hot water (at 85° C. for 30 minutes)→(6) a step of washing with a 1% aqueous solution of a surfactant→(7) a step of washing with hot water (at 85° C. for 30 minutes).

The manufacturing and packaging system was subjected to washing procedures according to the foregoing protocol, after the formation of juices, whose odor-threshold values are low, such as apple juice (principal flavoring components thereof comprising, for instance, esters such as methyl 2-methyl butanoate, 3-methylbutyl and 3-methylhexyl): peach juice (principal flavoring components thereof comprising, for instance, lactones such as 4-butylbutanolide, and γ-caprolactone); and grape fruit juice (principal flavoring components thereof comprising, for instance, aldehydes such as octanal and decanal). However, the foregoing washing steps should continuously be repeated over 5 to 10 cycles, till all of the 5 panels who had quite sharp olfactory sense and the sense of taste judged that the manufacturing and packaging system was completely tasteless and odorless.

Example 22

After the production of apple juice in the factory described in Comparative Example 11, the production system was, only once, subjected to washing procedure according to the foregoing step (6) except that the step (6) was carried out at 85° C. for 30 minutes, while the surfactant aqueous solution used in the step (6) was replaced with aqueous solution prepared by dissolving, in water, 0.001% of a sol of amphoteric poly(acrylamide) used in Example 1, as expressed in terms of the solid content thereof, 0.0033% of poly(methylene-biguanide) hydrochloride, as expressed in terms of the anhydride thereof, 0.009% of di-isopropylene glycol; 0.009% of tri-isopropanolamine salt of oleic acid; 0.02% of methyl propylene glycol; 0.0013% of 2-ethylhexyl alcohol; and 0.027% of sodium sulfate in terms of the anhydride thereof. At this stage, 5 panels were requested to make judgment and as a result, the production system thus washed was found to be completely tasteless and odorless. For this reason, another kind of refreshing beverage could immediately be produced.

What is claimed is:

1. A cleaning agent comprising (A) an aqueous solution or an aqueous dispersion containing a linear poly(meth)acrylamide having an average molecular weight of not less than $5\times10^6$ as determined according to the intrinsic viscosity-determining technique in a concentration ranging from 0.0001 to 0.01% by mass; (B) a poly(polymethylene-biguanide) hydrochloride represented by the following general formula (1); and (C) at least one compound selected from the group consisting of propylene glycol, dipropylene glycol, tripropylene glycol, and glycine:

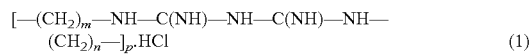

(1)

wherein m and n each represent an integer ranging from 2 to 5 and p is an integer ranging from 5 to 16.

2. The cleaning agent as set forth in claim 1, wherein the aqueous solution or aqueous dispersion of poly(meth)acrylamide (A) is one whose solid content increases when drying the same to thus form a water-retentive gel.

3. The cleaning agent as set forth in claim 1, wherein the compound (C) is glycine.

4. The cleaning agent as set forth in claim 1, wherein the poly(meth)acrylamide is an amphoteric charged polymer.

5. The cleaning agent as set forth in claim 1, wherein it comprises a water-soluble acrylic copolymer.

6. The cleaning agent as set forth in claim 5, wherein the water-soluble acrylic copolymer is an ammonium salt of (meth)acrylic acid- (meth)acrylate copolymer.

7. The cleaning agent as set forth in claim 1, wherein it comprises water-soluble inorganic salt.

8. The cleaning agent as set forth in claim 1, wherein it comprises a gelling agent.

9. The cleaning agent as set forth in claim 8, wherein the gelling agent is at least one member selected from the group consisting of water-soluble alkali metal salts; water-soluble divalent alkaline earth metal salts; aluminum compounds; dibasic carboxylic acids having 2 to 18 carbon atoms and ammonium salts, amine salts and amino-alcohol salts thereof; di-hydrazides of water-soluble high molecular weight compounds; glytaraldehyde; and glyoxal.

10. The cleaning agent as set forth in claim 8, wherein, when the poly(meth)acrylamide is a negatively charged polymer or a positively charged polymer, the gelling agent is an aqueous solution of salts of oppositely charged poly(meth)acrylamide and/or another high molecular weight compound, in any case.

11. The cleaning agent as set forth in claim 1, wherein it comprises a fatty acid salt or a derivative thereof.

12. The cleaning agent as set forth in claim 1, wherein it comprises any one of quaternary ammonium salt, glycol ether or crown ether, as a phase transfer catalyst.

13. The cleaning agent as set forth in claim 1, wherein it comprises an alcohol amine having 4 to 12 carbon atoms.

14. The cleaning agent as set forth in claim 1, wherein it comprises a magnetic substance.

15. The cleaning agent as set forth in claim 14, wherein the magnetic substance is at least one member selected from the group consisting of very fine powdery iron, cobalt, nickel, magnetite, or a magnetic fluid each obtained by dispersing either of the foregoing metals with the aid of a surfactant.

* * * * *